US010667684B2

(12) United States Patent
Shibutani et al.

(10) Patent No.: US 10,667,684 B2
(45) Date of Patent: Jun. 2, 2020

(54) OCT APPARATUS

(71) Applicant: TOPCON CORPORATION, Itabashi-ku, Tokyo (JP)

(72) Inventors: Masahiro Shibutani, Kawaguchi (JP); Ryoichi Hirose, Itabashi (JP); Toshihiro Mino, Warabi (JP)

(73) Assignee: TOPCON CORPORATION, Itabashi-ku, Tokyo (JP)

(*) Notice: Subject to any disclaimer, the term of this patent is extended or adjusted under 35 U.S.C. 154(b) by 359 days.

(21) Appl. No.: 15/670,234

(22) Filed: Aug. 7, 2017

(65) Prior Publication Data
US 2018/0084991 A1    Mar. 29, 2018

(30) Foreign Application Priority Data

Sep. 23, 2016  (JP) .................................. 2016-185220

(51) Int. Cl.
*A61B 3/10*    (2006.01)
*A61B 3/00*    (2006.01)
*A61B 3/15*    (2006.01)

(52) U.S. Cl.
CPC ............ *A61B 3/102* (2013.01); *A61B 3/0025* (2013.01); *A61B 3/0033* (2013.01); *A61B 3/152* (2013.01)

(58) Field of Classification Search
CPC ..... A61B 3/102; A61B 3/0025; A61B 3/0033; A61B 3/152; A61B 3/1025; A61B 3/12; A61B 3/1233; A61B 3/1241; A61B 3/14; A61B 3/145
USPC ....................................................... 351/206
See application file for complete search history.

(56) References Cited

U.S. PATENT DOCUMENTS

| 2011/0228218 A1* | 9/2011 | Hauger | A61B 3/102 |
| | | | 351/205 |
| 2012/0033181 A1* | 2/2012 | Koizumi | A61B 3/102 |
| | | | 351/208 |

FOREIGN PATENT DOCUMENTS

JP    2015070919 A    4/2015

OTHER PUBLICATIONS

S. Witte et al., "Single-shot two-dimensional full-range optical coherence tomography achieved by dispersion control," Optics Express, Jul. 6, 2009, vol. 17 (No. 14), pp. 11335-11349.

* cited by examiner

*Primary Examiner* — William R Alexander
*Assistant Examiner* — Henry A Duong
(74) *Attorney, Agent, or Firm* — Chiesa Shahinian & Giantomasi PC

(57) ABSTRACT

An optical coherence tomography (OCT) apparatus according to an embodiment is configured to split light from a light source into measurement light and reference light, project the measurement light on an object, and detect interference light generated from the reference light and the measurement light returning from the object. The OCT apparatus includes a dispersion unit and an information generation unit. The dispersion unit is configured to relatively change a dispersion characteristic of a measurement optical path which is an optical path of the measurement light and a dispersion characteristic of a reference optical path which is an optical path of the reference light, according to an operation mode corresponding to a depth range. The information generation unit is configured to generate information on the object according to the operation mode, based on a detection result of the interference light.

20 Claims, 16 Drawing Sheets

US 10,667,684 B2

OCT APPARATUS

CROSS-REFERENCE TO RELATED APPLICATION

This application is based upon and claims the benefit of priority from Japanese Patent Application No. 2016-185220, filed Sep. 23, 2016, the entire contents of which are incorporated herein by reference.

BACKGROUND

In recent years, attention has been drawn to optical coherence tomography (OCT) which is used to form images representing the surface morphology and the internal morphology of an object using light beams emitted from a laser light source or the like. Since OCT does not have invasiveness to human body as X-ray CT (Computed Tomography) does, development of application of OCT in medical field and biology field is particularly expected. For example, in the field of ophthalmology, OCT apparatuses have been put to practical use for forming images of the fundus, the cornea, etc. and measuring the intraocular distance such as the axial length.

It is known that various artifacts are mixed in the image of an object obtained using OCT. In particular, the complex conjugate artifact is depicted in the image acquired with Fourier domain OCT. The complex conjugate artifact is the imaginary image that appears on the opposite side of the real image with respect to the zero delay position where the optical path length (OPL) of the measurement light applied to the object is equal to the optical path length of the reference light. For example, by forming a cross sectional image from the real image that appears on one side of the range (e.g., on the plus range) with respect to the zero delay position, it is possible to acquire a cross sectional image of the object with high image quality in a narrow depth range. Also, for example, by removing the complex conjugate artifact to form a cross sectional image, it is possible to acquire a cross sectional image of the object in the full range.

A method for acquiring a cross sectional image of an object in the full range by removing the complex conjugate artifact is disclosed, for example, in the following document: S. Witte, M. Baclayon, E. J. G. Peterman, R. F. G. Toonen, H. D. Mansvelder, and M. L. Groot, "Single-shot two-dimensional full-range optical coherence tomography achieved by dispersion control", OPTICS EXPRESS, Jul. 6, 2009, Vol. 17 (No. 14), pp. 11335-11349.

SUMMARY

An optical coherence tomography (OCT) apparatus according to an embodiment is configured to split light from a light source into measurement light and reference light, project the measurement light on an object, and detect interference light generated from the reference light and the measurement light returning from the object. The OCT apparatus includes a dispersion unit and an information generation unit. The dispersion unit is configured to relatively change a dispersion characteristic of a measurement optical path which is an optical path of the measurement light and a dispersion characteristic of a reference optical path which is an optical path of the reference light, according to an operation mode corresponding to a depth range. The information generation unit is configured to generate information on the object according to the operation mode, based on a detection result of the interference light.

DETAILED DESCRIPTION

Exemplary embodiments of the OCT apparatus according to the present invention will be described in detail with reference to the drawings. The contents of the documents cited in the present specification and arbitrary known techniques can be incorporated into the following embodiments.

The OCT apparatus according to the present embodiment has at least a function of performing OCT. The OCT apparatus is a measurement apparatus capable of acquiring information on an object by performing OCT on the object. Hereinafter, a case will be described where the OCT apparatus according to the present embodiment is an ophthalmic apparatus that acquires cross sectional images of a living eye by performing OCT on the living eye that is an object to be measured. However, embodiments are not limited thereto. For example, the OCT apparatus according to an embodiment may be an ophthalmic apparatus capable of measuring the intraocular distance of a living eye such as the axial length by performing OCT on the living eye.

The OCT apparatus according to the present embodiment is an ophthalmic apparatus that is a combination of a Fourier domain OCT apparatus and a fundus camera. The OCT apparatus has a function of performing swept source OCT, but embodiments are not limited to this. For example, the type of OCT is not limited to swept source OCT, and it may be the spectral domain OCT or the like. The swept source OCT is an OCT technique that splits light from a wavelength tunable type (i.e., a wavelength scanning type) light source into measurement light and reference light; superposes the measurement light returning from the object with the reference light to generate interference light; detects the interference light with a balanced photodiode or the like; and applies the Fourier transform etc. to the detection data acquired through the tuning of wavelengths and the scanning of the measurement light to form an image. On the other hand, spectral domain OCT is an OCT technique that splits light from a low coherence light source into measurement light and reference light; superposes the measurement light returning from the object with the reference light to generate interference light; detects the spectral distribution of the interference light with a spectrometer; and applies the Fourier transform etc. to the detected spectral distribution to form images.

The OCT apparatus according to the present embodiment may include a scanning laser ophthalmoscope (SLO), a slit lamp microscope, an anterior segment photographing camera, a surgical microscope, a photocoagulator, etc. in place of or in addition to the fundus camera. In the present specification, an image acquired using OCT is referred to as an OCT image. The optical path of the measurement light is denoted as a "measurement optical path", and the optical path of the reference light is denoted as a "reference optical path".

[Configuration]

Figure 1:
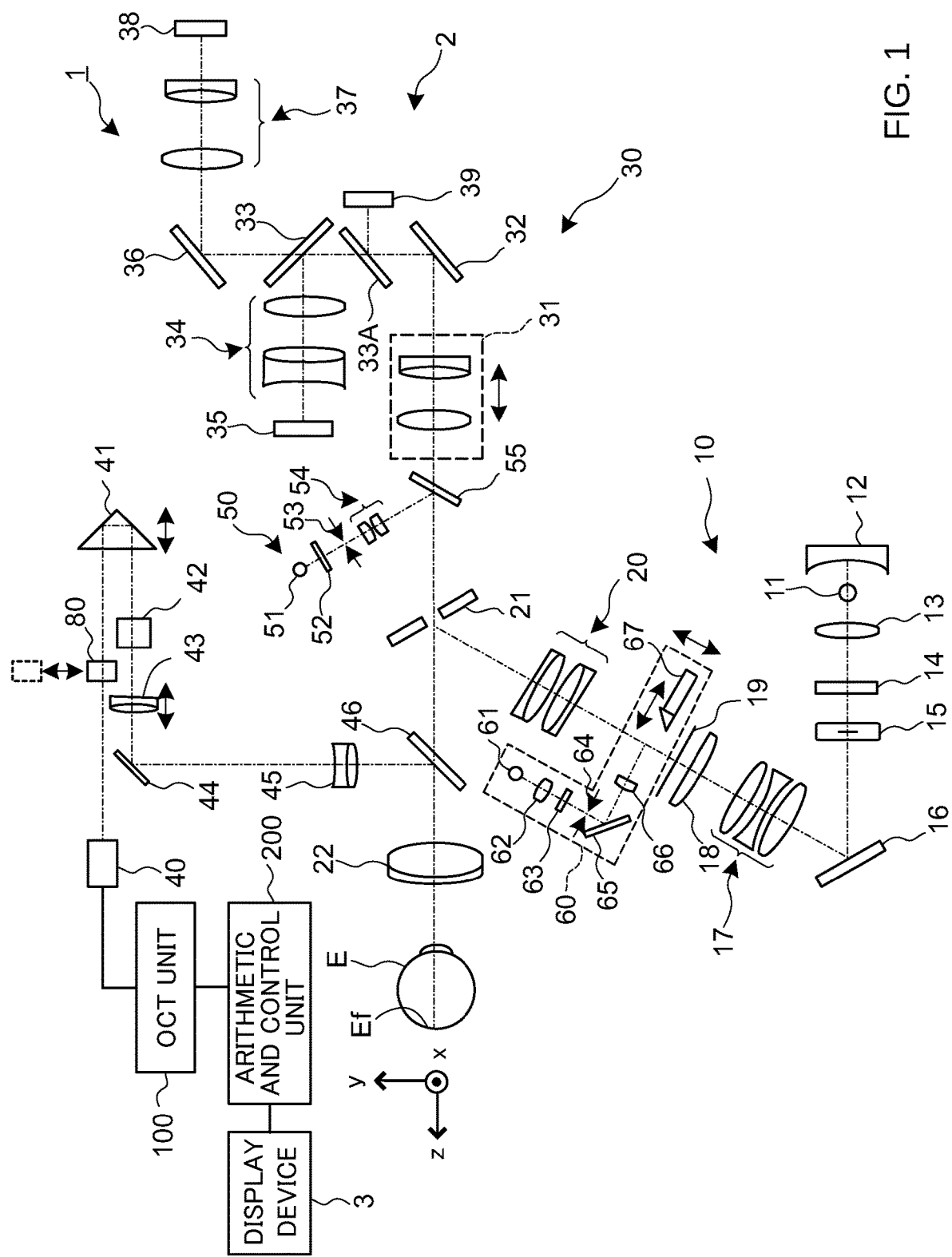
FIG. 1 is a schematic diagram illustrating an example of the configuration of an optical system of an OCT apparatus according to an embodiment.

The ophthalmic apparatus 1 shown in FIG. 1 includes the OCT apparatus according to the present embodiment. The ophthalmic apparatus 1 includes the fundus camera unit 2, the OCT unit 100, and the arithmetic and control unit 200. The fundus camera unit 2 has substantially the same optical system as the conventional fundus camera. The OCT unit 100 is provided with an optical system for performing OCT. The arithmetic and control unit 200 is provided with one or more processors for performing various kinds of arithmetic processing, control processing, and the like.

In the present specification, the term "processor" is used to mean, for example, a circuity including a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), or the like. The processor realizes the function according to the present embodiment, for example, by read out a computer program stored in a storage circuit or a storage device and executing the computer program.

[Fundus Camera Unit]

The fundus camera unit 2 is provided with an optical system for acquiring two dimensional images (fundus images) rendering the surface morphology of the fundus Ef of the subject's eye E. Examples of the fundus images include observation images and photographed images. An observation image is, for example, a monochrome moving image formed at a predetermined frame rate using near-infrared light. A photographed image is, for example, a color image captured by flashing visible light, or a monochrome still image using near-infrared light or visible light as illumination light. The fundus camera unit 2 may be configured to be capable of acquiring other types of images such as fluorescein angiograms, indocyanine green angiograms, and autofluorescent angiograms.

The fundus camera unit 2 is provided with a jaw holder and a forehead rest for supporting the face of the subject. In addition, the fundus camera unit 2 is provided with the illumination optical system 10 and the photographing optical system 30. The illumination optical system 10 projects illumination light onto the fundus Ef. The photographing optical system 30 guides the illumination light reflected from the fundus Ef to an imaging device (i.e., the CCD image sensors 35 or 38). Each of the CCD image sensors 35 and 38 is sometimes simply referred to as a "CCD". Further, the photographing optical system 30 guides measurement light coming from the OCT unit 100 to the subject's eye E, and guides the measurement light returning from the subject's eye E to the OCT unit 100.

The observation light source 11 of the illumination optical system 10 includes, for example, a halogen lamp or a light emitting diode (LED). The light (observation illumination light) output from the observation light source 11 is reflected by the reflection mirror 12 having a concave reflective surface, passes through the condenser lens 13, and becomes near-infrared light after passing through the visible cut filter 14. Further, the observation illumination light is once converged near the photographing light source 15, reflected by the mirror 16, and passes through the relay lenses 17 and 18, the diaphragm 19, and the relay lens 20. Then, the observation illumination light is reflected on the peripheral part (the surrounding area of the aperture part) of the aperture mirror 21, penetrates the dichroic mirror 46, and refracted by the objective lens 22, thereby illuminating the fundus Ef.

The observation illumination light reflected from the fundus Ef is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the fundus reflection light passes through the half mirror 33A, is reflected by the dichroic mirror 33, and forms an image on the light receiving surface of the CCD image sensor 35 by the condenser lens 34. The CCD image sensor 35 detects the fundus reflection light at a predetermined frame rate, for example. An image (observation image) based on the fundus reflection light detected by the CCD image sensor 35 is displayed on the display device 3. Note that when the focus of the photographing optical system 30 is adjusted to the anterior segment of the subject's eye E, an observation image of the anterior segment of the subject's eye E is acquired and displayed.

The photographing light source 15 is formed of, for example, a xenon lamp or an LED. The light (photographing illumination light) output from the photographing light source 15 is guided to the fundus Ef along the same route as that of the observation illumination light. The photographing illumination light reflected from the fundus Ef is guided to the dichroic mirror 33 along the same route as that of the observation illumination light, passes through the dichroic mirror 33, is reflected by the mirror 36, and forms an image on the light receiving surface of the CCD image sensor 38 by the condenser lens 37. The display device 3 displays an image (photographed image) based on the fundus reflection light detected by the CCD image sensor 38. Note that the same device or different devices may be used for the display device 3 for displaying observation images and the display device 3 for displaying photographed images. Besides, when similar photography is performed by illuminating the subject's eye E with infrared light, an infrared photographed image is displayed.

The liquid crystal display (LCD) 39 displays a fixation target and a visual target used for visual acuity measurement.

The fixation target is a visual target for fixating the subject's eye E, and is used when performing fundus photography and OCT measurement.

Part of the light output from the LCD 39 is reflected by the half mirror 33A, reflected by the mirror 32, travels through the photography focusing lens 31 and the dichroic mirror 55, and passes through the aperture part of the aperture mirror 21. The light passed through the aperture part of the aperture mirror 21 penetrates the dichroic mirror 46, and is refracted by the objective lens 22, thereby being projected onto the fundus Ef. By changing the display position of the fixation target on the screen of the LCD 39, the fixation position of the subject's eye E can be changed.

In addition, as with a conventional fundus camera, the fundus camera unit 2 is provided with the alignment optical system 50 and the focus optical system 60. The alignment optical system 50 generates an indicator (referred to as an alignment indicator) for the position adjustment (i.e., the alignment) of the optical system with respect to the subject's eye E. The focus optical system 60 generates an indicator (referred to as a split indicator) for adjusting the focus of the photographing optical system 30 with respect to the subject's eye E.

The light output from an LED 51 of the alignment optical system 50 (i.e., alignment light) travels through the diaphragms 52 and 53 and the relay lens 54, is reflected by the dichroic mirror 55, and passes through the aperture part of the aperture mirror 21. The alignment light passed through the aperture part of the aperture mirror 21 penetrates the dichroic mirror 46, and is projected onto the cornea of the subject's eye E by the objective lens 22.

The alignment light reflected from the cornea travels through the objective lens 22, the dichroic mirror 46 and the above-mentioned aperture part. Part of the cornea reflection light penetrates the dichroic mirror 55 and passes through the photography focusing lens 31. The cornea reflection light passed through the photography focusing lens 31 is reflected by the mirror 32, penetrates the half mirror 33A, is reflected by the dichroic mirror 33, and is projected onto the light receiving surface of the CCD image sensor 35 by the condenser lens 34. The received image (i.e., alignment indicator image) captured by the CCD image sensor 35 is displayed on the display device 3 together with the observation image. The user conducts an alignment operation in the same manner as performed on a conventional fundus camera. Instead, alignment may be performed in such a way that the arithmetic and control unit 200 analyzes the position of the alignment indicator image and moves the optical system (automatic alignment).

The focus optical system 60 is movable along the optical path of the illumination optical system 10 in conjunction with the movement of the photography focusing lens 31 along the optical path of the photographing optical system 30. The reflection rod 67 of the focus optical system 60 can be inserted and removed into and from the illumination optical path.

To conduct focus adjustment, the reflective surface of the reflection rod 67 is arranged in a slanted position on the illumination optical path. The light output from the LED 61 of the focus optical system 60 (i.e., focus light) passes through the relay lens 62, is split into two light beams by the split indicator plate 63, passes through the two-hole diaphragm 64. The focus light passed through the two-hole diaphragm 64 is reflected by the mirror 65, is converged on the reflective surface of the reflection rod 67 by the condenser lens 66, and is reflected by the reflective surface. Further, the focus light travels through the relay lens 20, is reflected by the aperture mirror 21, penetrates the dichroic mirror 46, and is refracted by the objective lens 22, thereby being projected onto the fundus Ef.

The focus light reflected from the fundus is guided along the same route as the alignment light reflected from the cornea and is detected by the CCD image sensor 35. The received image (i.e., split indicator image) captured by the CCD image sensor 35 is displayed on the display device 3 together with the observation image. As in the conventional case, the arithmetic and control unit 200 can analyze the position of the split indicator image, and move the photography focusing lens 31 and the focus optical system 60 for the focus adjustment (automatic focusing). Instead, the user may manually perform the focus adjustment while visually checking the split indicator image.

The reflection rod 67 is inserted at a position on the illumination optical path substantially optically conjugate with the fundus Ef of the subject's eye E. The position of the reflective surface of the reflection rod 67 inserted in the optical path of the illumination optical system 10 is a position substantially optically conjugate with the split indicator plate 63. As described above, the split indicator light beam is split into two beams by the action of the two-hole diaphragm 64 and the like. When the fundus Ef of the subject's eye E and the reflective surface of the reflection rod 67 are not conjugate, two split indicator images acquired by the CCD image sensor 35 are displayed on the display device 3 in such a way that the split indicator images are separated in the right-and-left direction, for example. When the fundus Ef of the subject's eye E and the reflective surface of the reflection rod 67 are substantially optically conjugate with each other, the two split indicator images are displayed on the display device 3 in such a way that the positions of the split indicator images acquired by the CCD image sensor 35 coincide with each other in the vertical direction, for example. The focus optical system 60 is moved along the optical path of the illumination optical system 10 in conjunction with the movement of the photography focusing lens 31 so that the fundus Ef and the split indicator plate 63 are always optically conjugate with each other. When the fundus Ef and the split indicator plate 63 are not conjugate, the split indicator image is separated into two. Thus, the position of the photography focusing lens 31 is obtained by moving the focus optical system 60 so that the two split indicator images coincide with each other in the vertical direction. In the present embodiment, the case where two split indicator images are acquired has been described, but the number of split indicator images may be three or more.

The dichroic mirror 46 branches the optical path for OCT from the optical path for fundus photography. The dichroic mirror 46 reflects light of wavelengths used in OCT, and transmits light for fundus photography. The optical path for OCT is provided with, in order from the OCT unit 100 side, the collimator lens unit 40, the optical path length (OPL) changing unit 41, the optical scanner 42, the OCT focusing lens 43, the mirror 44, and the relay lens 45.

The collimator lens unit 40 includes a collimator lens. The collimator lens unit 40 is optically connected to the OCT unit 100 with an optical fiber. A collimator lens in the collimator lens unit 40 is disposed at a position facing the emitting end of the optical fiber. The collimator lens unit 40 converts the measurement light LS (described later) emitted from the emitting end of the optical fiber into a parallel light beam and converges the returning light of the measurement light LS from the subject's eye E to the emitting end of the optical fiber.

The optical path length changing unit 41 is movable in directions indicated by the arrow in FIG. 1, thereby changing the length of the optical path for OCT measurement. The change in the optical path length is used for correcting the optical path length according to the axial length of the subject's eye E, for adjusting the interference state, and the like. The optical path length changing unit 41 includes, for example, a corner cube and a mechanism for moving the corner cube.

The optical scanner 42 is disposed at a position optically conjugate with the pupil of the subject's eye E. The optical scanner 42 changes the traveling direction of the light (measurement light LS) traveling along the OCT optical path. With this, the subject's eye E can be scanned with the measurement light LS. The optical scanner 42 includes, for example, a galvano mirror that deflects the measurement light LS in the x direction, a galvano mirror that deflects the measurement light LS in the y direction, and a mechanism(s) that independently drives the galvano mirrors. With this, it is possible to scan the measurement light LS in an arbitrary direction in the xy plane.

The dispersion member 80 is inserted into and removed from the measurement optical path between the collimator lens unit 40 and the optical scanner 42. The dispersion member 80 gives a predetermined dispersion amount to the measurement optical path. The dispersion amount increases the difference between the dispersion characteristic of the measurement optical path and the dispersion characteristic of the reference optical path described later. Specifically, the dispersion amount may be equal to or larger than 30n radians when the optical path length difference caused by chromatic dispersion between the reference optical path and the measurement optical path is converted into a phase difference. For the dispersion member 80 as such, a glass material of a kind and a thickness corresponding to the dispersion amount is used. In the present embodiment, the dispersion member 80 is inserted into and removed from the measurement optical path in accordance with the operation mode corresponding to the depth range of the ophthalmic apparatus 1.

[OCT Unit]

Figure 2:
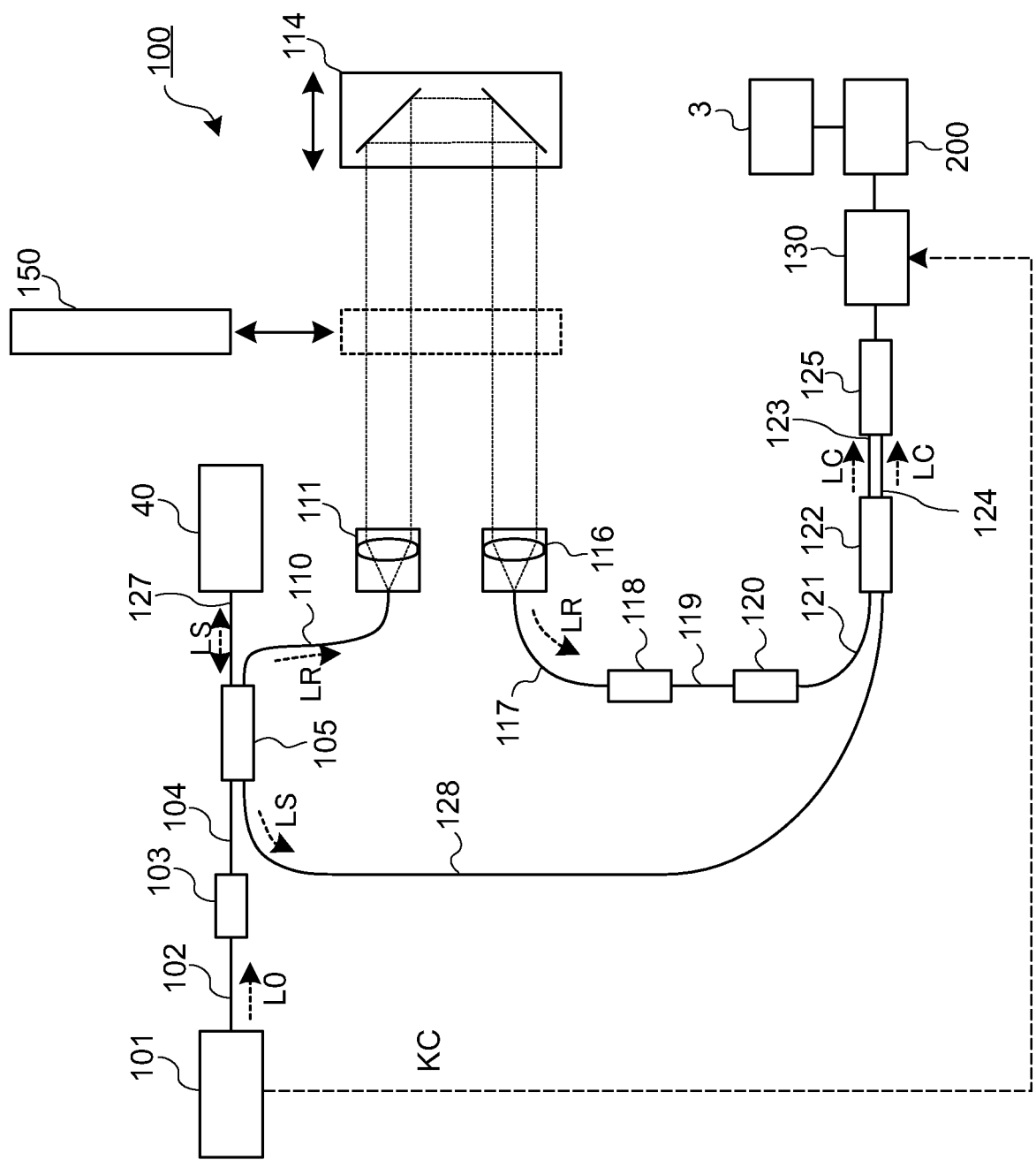
FIG. 2 is a schematic diagram illustrating an example of the configuration of an optical system of the OCT apparatus according to the embodiment.

An example of the configuration of the OCT unit 100 is shown in FIG. 2. The OCT unit 100 includes an optical system for acquiring OCT images of the subject's eye E. The optical system includes an interference optical system (i.e., interferometer) that splits the light from a wavelength tunable type (i.e., a wavelength scanning type) light source into measurement light and reference light, makes the measurement light returning from the subject's eye E and the reference light having traveled through the reference optical path interfere with each other to generate interference light, and detects the interference light. The detection result of the interference light obtained by the interference optical system (i.e., the detection signal) is an interference signal indicating the spectrum of the interference light, and is sent to the arithmetic and control unit 200.

Like swept source OCT apparatuses commonly used, the light source unit 101 includes a wavelength tunable type (i.e., a wavelength scanning type) light source capable of sweeping (scanning) the wavelengths of emitted light. The wavelength tunable type light source includes a laser light source that includes a resonator. The light source unit 101 temporally changes the output wavelengths within the near infrared wavelength bands that cannot be visually recognized with human eyes.

The light L0 output from the light source unit 101 is guided to the polarization controller 103 through the optical fiber 102 and the polarization state thereof is adjusted. The polarization controller 103, for example, applies external stress to the looped optical fiber 102 to thereby adjust the polarization state of the light L0 guided through the optical fiber 102.

The light L0 whose polarization state has been adjusted by the polarization controller 103 is guided to the fiber coupler 105 through the optical fiber 104 and is split into the measurement light LS and the reference light LR.

The reference light LR is guided to the collimator 111 through the optical fiber 110 and becomes a parallel light beam. The reference light LR, which has become a parallel light beam, is guided to the corner cube 114. The corner cube 114 changes the traveling direction of the reference light LR that has been made into the parallel light beam by the collimator 111 in the opposite direction. The optical path of the reference light LR incident on the corner cube 114 and the optical path of the reference light LR emitted from the corner cube 114 are parallel. Further, the corner cube 114 is movable in a direction along the incident light path and the emitting light path of the reference light LR. Through such movement, the length of the optical path of the reference light LR is varied.

The configuration shown in FIG. 1 and FIG. 2 includes both the optical path length changing unit 41 that changes the length of the optical path of the measurement light LS (i.e., measurement optical path or measurement arm) and the corner cube 114 that changes the length of the optical path of the reference light LR (i.e., reference optical path or reference arm). However, an OCT apparatus of another embodiment may include the corner cube 114 only. An OCT apparatus of yet another embodiment may be configured to change the difference between the measurement optical path length and the reference optical path length using another kind of optical member.

The reference light LR that has traveled through the corner cube 114 is converted from the parallel light beam to the convergent light beam by the collimator 116 and enters the optical fiber 117. The dispersion member 150 is inserted into and removed from at least one of the reference optical path between the collimator 111 and the corner cube 114 and the reference optical path between the collimator 116 and the corner cube 114. The dispersion member 150 gives a predetermined dispersion amount to the reference optical path. The dispersion amount, for example, compensates for the difference between the dispersion characteristic of the measurement optical path in which the dispersion member 80 is not disposed and the dispersion characteristic of the reference optical path. For the dispersion member 150 as such, a glass material of a kind and a thickness corresponding to the dispersion amount is used. In the present embodiment, the dispersion member 150 is inserted into and removed from the reference optical path in accordance with the operation mode of the ophthalmic apparatus 1.

An optical path length correction member may be disposed in at least one of the reference optical path between the collimator 111 and the corner cube 114 and the reference optical path between the collimator 116 and the corner cube 114. The optical path length correction member functions as a delaying means for matching the optical path length (i.e., optical distance) of the reference light LR with the optical path length of the measurement light LS.

The reference light LR that has entered the optical fiber 117 is guided to the polarization controller 118. With the polarization controller 118, the polarization state of the reference light LR is adjusted. The polarization controller 118 has the same configuration as, for example, the polarization controller 103. The reference light LR whose polarization state has been adjusted by the polarization controller 118 is guided to the attenuator 120 through the optical fiber 119 and the light amount is adjusted by the attenuator 120 under the control of the arithmetic and control unit 200. The reference light LR whose light amount is adjusted by the attenuator 120 is guided to the fiber coupler 122 through the optical fiber 121.

Meanwhile, the measurement light LS generated by the fiber coupler 105 is guided through the optical fiber 127, and is made into the parallel light beam by the collimator lens unit 40. When the dispersion member 80 is not disposed in the measurement optical path, the measurement light LS made into the parallel light beam is guided to the dichroic mirror 46 via the optical path length changing unit 41, the optical scanner 42, the OCT focusing lens 43, the mirror 44, and the relay lens 45. When the dispersion member 80 is disposed in the measurement optical path, the measurement light LS made into the parallel light beam is guided to the dichroic mirror 46 via the dispersion member 80, the optical path length changing unit 41, the optical scanner 42, the OCT focusing lens 43, the mirror 44, and the relay lens 45. The measurement light LS guided to the dichroic mirror 46 is reflected by the dichroic mirror 46, refracted by the objective lens 22, and projected onto the subject's eye E. The measurement light LS is scattered (and reflected) at various depth positions of the subject's eye E. The returning light of the measurement light LS including such backscattered light advances through the same path as the outward path in the opposite direction and is led to the fiber coupler 105, and then reaches the fiber coupler 122 through the optical fiber 128.

The fiber coupler 122 superposes the measurement light LS incident through the optical fiber 128 and the reference light LR incident through the optical fiber 121 with each other to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 is guided to a detector 125 through optical fibers 123 and 124, respectively.

The detector 125 is, for example, a balanced photodiode that includes a pair of photodetectors for respectively detecting the pair of the interference light LC and outputs the difference between the pair of detection results obtained by the pair of photodetectors. The detector 125 sends the detection result (i.e., interference signal) to the data acquisition system (DAQ) 130. The clock KC is supplied from the light source unit 101 to the DAQ 130. The clock KC is generated in the light source unit 101 in synchronization with the output timing of each wavelength sweeping (i.e., wavelength scanning) within a predetermined wavelength range performed by the wavelength tunable type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs the sampling of the detection result obtained by the detector 125 based on the clock KC. The DAQ 130 sends the result of the sampling of the detection result obtained by the detector 125 to the arithmetic and control unit 200. For example, the arithmetic and control unit 200 performs the Fourier transform etc. on the spectral distribution based on the detection result obtained by the detector 125 for each series of wavelength scanning (i.e., for each A line). With this, the reflection intensity profile for each A line is formed. In addition, the arithmetic and control unit 200 forms image data by applying imaging processing to the reflection intensity profiles of the respective A lines.

[Arithmetic and Control Unit]

The configuration of the arithmetic and control unit 200 will be described. The arithmetic and control unit 200 analyzes the interference signals input from the detector 125 to form an OCT image of the subject's eye E. The arithmetic processing for forming an OCT image corresponding to a depth range narrower than the full range is executed in the same manner as the conventional swept source OCT.

In addition, the arithmetic and control unit 200 controls each part of the fundus camera unit 2, the display device 3, and the OCT unit 100. For example, the arithmetic and control unit 200 controls the display device 3 to display the OCT image of the subject's eye E.

Like conventional computers, the arithmetic and control unit 200 includes a microprocessor, a random access memory (RAM), a read only memory (ROM), a hard disk drive, a communication interface, and the like. A storage device such as the hard disk drive stores a computer program for controlling the ophthalmic apparatus 1. The arithmetic and control unit 200 may include various kinds of circuitry such as a circuit board for forming OCT images. In addition, the arithmetic and control unit 200 may include an operation device (or an input device) such as a keyboard and a mouse, and a display device such as an LCD.

[Control System]

Figure 3:
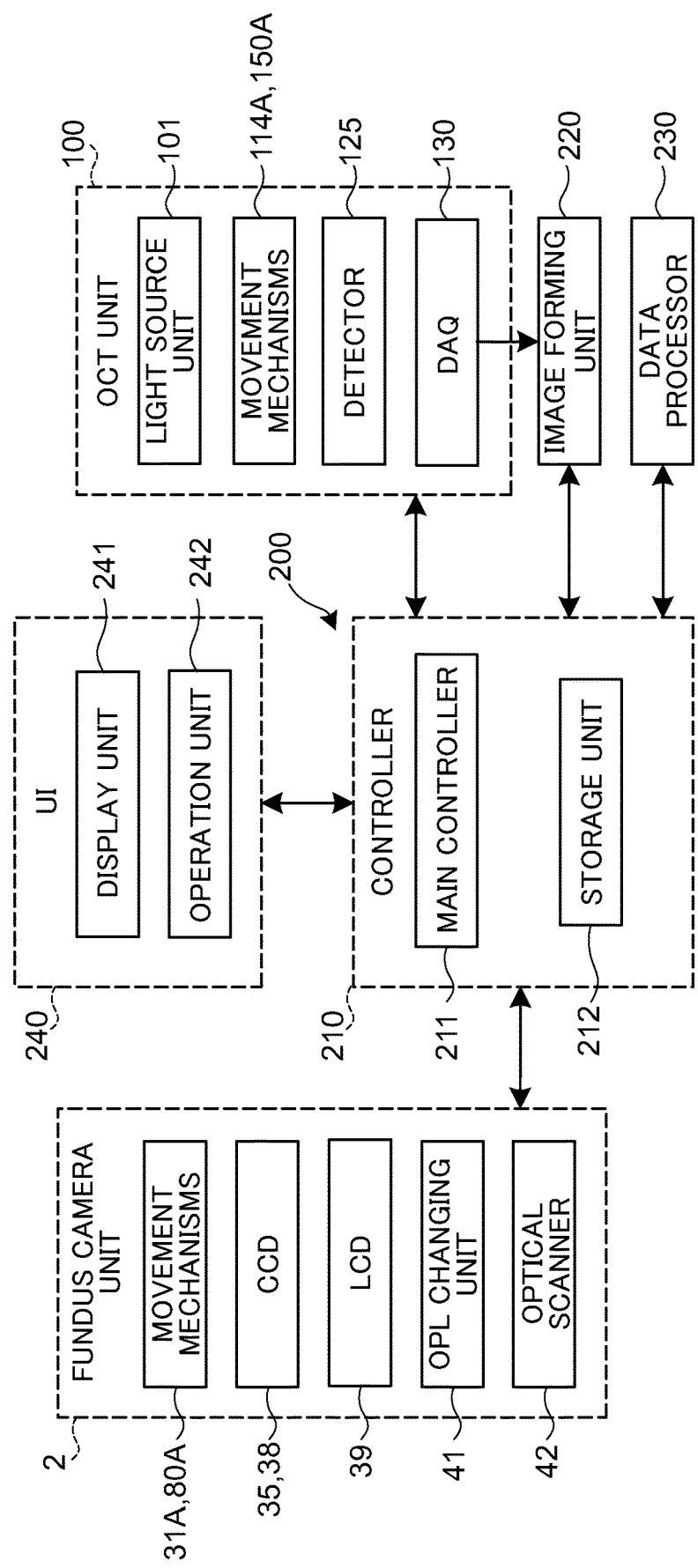
FIG. 3 is a schematic diagram illustrating an example of the configuration of a processing system of the OCT apparatus according to the embodiment.

The configuration of the control system of the ophthalmic apparatus 1 will be described with reference to FIG. 3. In FIG. 3, some components of the ophthalmic apparatus 1 are omitted, and the components particularly necessary for describing the present embodiment are selectively shown.

(Controller)

The arithmetic and control unit 200 includes the controller 210, the image forming unit 220, and the data processor 230. The controller 210 includes, for example, a microprocessor, a RAM, a ROM, a hard disk drive, a communication interface, and the like. The controller 210 is provided with the main controller 211 and the storage unit 212.

(Main Controller)

The main controller 211 performs various kinds of controls mentioned above. In particular, as shown in FIG. 3, the main controller 211 controls components of the fundus camera unit 2 such as the movement mechanisms 31A and 80A, the CCD image sensors 35 and 38, the LCD 39, the optical path length changing unit 41, and the optical scanner 42. In addition, the main controller 211 controls components of the OCT unit 100 such as the light source unit 101, the movement mechanisms 114A and 150A of, the detector 125, and the DAQ 130.

The ophthalmic apparatus 1 according to the present embodiment forms an OCT image corresponding to any of two or more operation modes corresponding to different depth ranges. The selection (or designation) of the operation mode may be performed by the main controller 211, or may be performed by the user operating the operation unit 242 described later. When the operation mode is selected by the main controller 211, the same operation mode as the previous operation may be selected, or the operation mode may be selected according to the object or the purpose of diagnosis.

In the present embodiment, operation mode options include a standard OCT mode and a full range OCT mode. The standard OCT mode is an operation mode for forming an OCT image with a high S/N ratio in a narrow depth range by using an interference signal appearing on one side of the range (i.e., on the plus range or the minus range) with respect to the zero delay position. The full range OCT mode is an operation mode for forming a full range OCT image by using both an interference signal on the plus range side and an interference signal on the minus range side. In the full range OCT mode, it is possible to acquire an OCT image that does not cause aliasing (that is, an OCT image that includes no mirror image), such as when acquiring a wide-angle cross sectional image of the subject's eye E or when the subject's eye E is of high myopia. In the standard OCT mode, for example, it is possible to acquire an OCT image with high image quality although the depth range in the standard mode is narrower than that in the full range. The standard OCT mode may also be selected when acquiring an OCT image in the vicinity of the zero delay position where the noise is superimposed in the full range.

The movement mechanism 31A moves the photography focusing lens 31 along the optical axis of the photographing optical system 30. The movement mechanism 31A is provided with a holding member that holds the photography focusing lens 31, an actuator that generates a driving force for moving the holding member, and a transmission mechanism that transmits the driving force from the actuator to the holding member. The actuator may be a pulse motor. The transmission mechanism may include a combination of gears, and a rack and pinion. As a result, the movement mechanism 31A controlled by the controller 210 moves the photography focusing lens 31, thereby the focus position of the photographing optical system 30 is changed. Note that the movement mechanism 31A may be configured to move the photography focusing lens 31 along the optical axis of the photographing optical system 30 in accordance with a manual operation or the user's operation on the operation unit 242.

Incidentally, the main controller 211 may be configured to control an optical system driver (not illustrated) to move the optical system of the ophthalmic apparatus 1 in the three dimensional manner. This control is used in alignment and tracking. Here, tracking is an operation of moving the optical system of the ophthalmic apparatus 1 according to the movement of the subject's eye E. To perform tracking, alignment and focusing are performed in advance. Tracking is a function of maintaining a suitable positional relationship in which alignment and focusing are matched, which is realized by moving the optical system of the apparatus in real time according to the position and orientation of the subject's eye E based on the moving image obtained by performing movie shoot of the subject's eye E.

The movement mechanism 80A inserts and removes the dispersion member 80 into and from the measurement optical path. The movement mechanism 80A is provided with a holding member that holds the dispersion member 80, an actuator that generates a driving force for moving the holding member, and a transmission mechanism that transmits the driving force from the actuator to the holding member. As a result, the movement mechanism 80A controlled by the controller 210 inserts and removes the dispersion member 80 into and from the measurement optical path. With this, the difference between the dispersion characteristic of the measurement optical path and the dispersion characteristic of the reference optical path is changed. Note that the movement mechanism 80A may be configured to insert and remove the dispersion member 80 into and from the measurement optical path according to a manual operation or the user's operation on the operation unit 242.

The movement mechanism 114A moves the corner cube 114 provided in the reference optical path. The movement mechanism 114A is provided with a holding member that holds the corner cube 114, an actuator that generates a driving force for moving the holding member, and a transmission mechanism that transmits the driving force from the actuator to the holding member. As a result, the length of the reference optical path is changed. Note that the movement mechanism 114A may be configured to move the corner cube 114 along the reference optical path according to a manual operation or the user's operation on the operation unit 242.

The movement mechanism 150A inserts and removes the dispersion member 150 into and from the reference optical path. The movement mechanism 150A is provided with a holding member that holds the dispersion member 150, an actuator that generates a driving force for moving the holding member, and a transmission mechanism that transmits the driving force from the actuator to the holding member. As a result, the movement mechanism 150A controlled by the controller 210 inserts and removes the dispersion member 150 into and from the reference optical path. With this, the difference between the dispersion characteristic of the measurement optical path and the dispersion characteristic of the reference optical path is changed. Note that the movement mechanism 150A may insert and remove the dispersion member 150 into and from the reference optical path according to a manual operation or the user's operation on the operation unit 242.

(Storage Unit)

The storage unit 212 stores various kinds of data. Examples of the data stored in the storage unit 212 include operation mode information of the ophthalmic apparatus 1, image data of an OCT image, image data of a fundus image, and subject's eye information. The subject's eye information includes information related to a subject such as patient ID and name, information related to a subject's eye such as identification information of left eye/right eye, and the like. In addition, the storage unit 212 stores various kinds of programs and various kinds of data to run the ophthalmic apparatus 1.

(Image Forming Unit)

The image forming unit 220 forms image data of a cross sectional image of the fundus Ef based on the interference signals from the detector 125 (i.e., from the DAQ 130) according to the operation mode. That is, the image forming unit 220 forms the image data of the subject's eye E based on the detection result of the interference light LC obtained by the interference optical system according to the operation mode. The image formation process includes noise removal (noise reduction), filtering, fast Fourier transform (FFT), and the like. The image data acquired in this manner is a data set including a group of image data formed by imaging the reflection intensity profiles of a plurality of A lines. Here, the plurality of A lines corresponds to the paths of the respective pieces of the measurement light LS in the eye E.

In order to improve the image quality, it is possible to repeatedly perform scan with the same pattern a plurality of times to collect a plurality of data sets, and to compose (e.g., to perform addition and average) the plurality of data sets.

Further, the image forming unit 220 forms an image in which two or more split indicator images are depicted from the image signal detected by the CCD 35 based on the returning light of two or more split indicators from the eye E that has passed through the photography focusing lens 31. Note that the main controller 211 may be configured to perform the formation of the image in which the two or more split indicator images are depicted.

The image forming unit 220 includes, for example, the circuitry described above. Note that "image data" and an "image" based on the image data may not be distinguished from each other in the present specification. In addition, a site of the subject's eye E and an image of the site may not be distinguished from each other.

(Data Processor)

The data processor 230 performs various kinds of data processing (e.g., image processing) and various kinds of analysis on an image formed by the image forming unit 220. For example, the data processor 230 performs various correction processes such as brightness correction and dispersion correction of images. The data processor 230 performs various kinds of image processing and analysis on images captured by the fundus camera unit 2 (e.g., fundus images, anterior segment images, etc.).

The data processor 230 can form volume data (voxel data) of the subject's eye E by performing known image processing such as interpolation processing for interpolating pixels between cross sectional images. In the case of displaying an image based on the volume data, the data processor 230 performs a rendering process on the volume data so as to form a pseudo three dimensional image viewed from a specific line-of-sight direction.

The data processor 230 can perform registration (i.e., position matching) between a fundus image and an OCT image. When the fundus image and the OCT image are obtained in parallel, the registration between the fundus image and the OCT image, which have been (almost) simultaneously obtained, can be performed using the optical axis of the photographing optical system 30 as a reference. Such registration can be achieved since the optical system for the fundus image and that for the OCT image are coaxial. Besides, regardless of the timing of obtaining the fundus image and that of the OCT image, the registration between a fundus image and an OCT image can be achieved by performing the registration between the fundus image with a front image formed by projecting at least part of the image area in the OCT image corresponding to the fundus Ef onto the xy plane. Such a registration technique can also be employed when the optical system for acquiring fundus images and the optical system for OCT are not coaxial. Further, when the optical system for acquiring fundus images and the optical system for OCT are not coaxial, if the relative positional relationship between these optical systems is known or can be detected, the registration can be performed with referring to the relative positional relationship in a similar manner to the case in which the optical systems are coaxial.

The data processor 230 that functions as above includes, for example, a microprocessor, a RAM, a ROM, a hard disk drive, a circuit board, and the like. The storage device such as the hard disk drive stores, in advance, a computer program for causing the microprocessor to execute the functions described above.

(User Interface)

The user interface 240 includes the display unit 241 and the operation unit 242. The display unit 241 includes the aforementioned display device of the arithmetic and control unit 200 and the display device 3. The operation unit 242 includes the aforementioned operation device of the arithmetic and control unit 200. The operation unit 242 may include various kinds of buttons and keys provided on the housing of the ophthalmic apparatus 1, or provided outside the ophthalmic apparatus 1. Further, the display unit 241 may include various kinds of display devices, such as a touch panel placed on the housing of the fundus camera unit 2.

Note that the display unit 241 and the operation unit 242 need not necessarily be formed as separate devices. For example, a device like a touch panel, which has a display function integrated with an operation function, can be used. In such a case, the operation unit 242 includes the touch panel and a computer program. The content of an operation performed using the operation unit 242 is fed to the controller 210 as an electrical signal. Moreover, operations and inputs of information may be performed using a graphical user interface (GUI) displayed on the display unit 241 and the operation unit 242.

Figure 4:
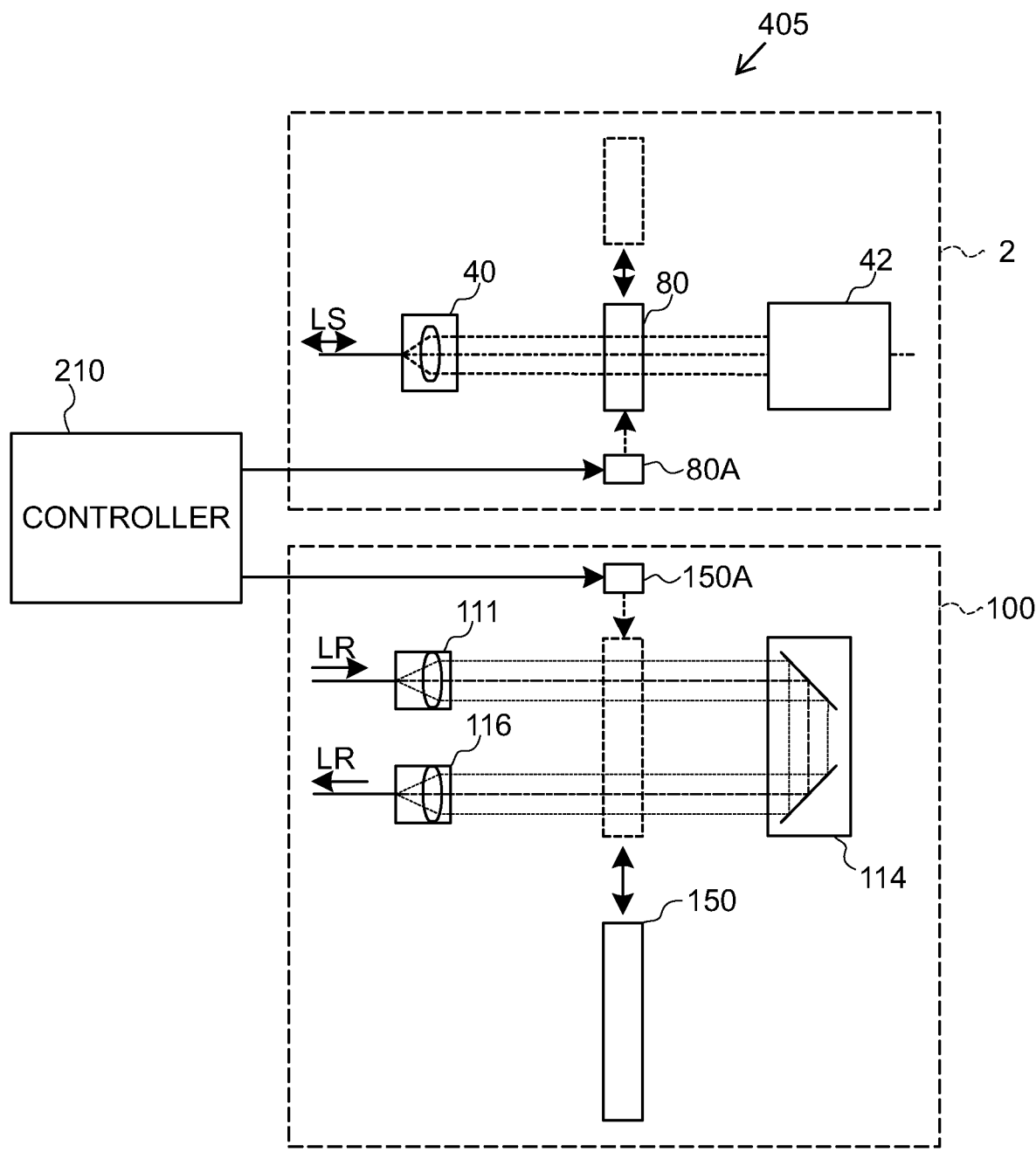
FIG. 4 is a diagram describing an operation of the OCT apparatus according to the embodiment.

FIG. 4 shows a diagram 405 describing the operation of the ophthalmic apparatus 1 according to the present embodiment. FIG. 4 schematically shows the arrangement states of the dispersion members 80 and 150 when the operation mode is set to the full range OCT mode. In FIG. 4, parts similar to those in FIG. 1 to FIG. 3 are denoted by the same reference symbols, and description thereof is omitted as appropriate.

When the operation mode is set to the standard OCT mode, the controller 210 (e.g., the main controller 211) controls the movement mechanism 80A to remove the dispersion member 80 from the measurement optical path, and controls the movement mechanism 150A to dispose the dispersion member 150 in the reference optical path. With this, the difference between the dispersion characteristic of the measurement optical path and the dispersion characteristic of the reference optical path is compensated. The measurement light LS generated based on the light L0 emitted from the light source unit 101 is projected onto the eye E as described above. The detector 125 receives the interference light LC, and the interference signal obtained by the detector 125 is sampled by the DAQ 130. The image forming unit 220 performs known numerical dispersion compensation processing on the sampled interference signal (i.e., spectra). Subsequently, the image forming unit 220 performs a known FFT process on the signal to which the dispersion compensation processing has been performed and assigns brightness values to the amplitude components generated based on the plus range side signal (or the minus range side signal) with respect to the zero delay position to form an OCT image. The image forming unit 220 may be configured to perform apodization processing using a window function such as known Hanning window or Gaussian window on the interference signal obtained by the detector 125 and perform the aforementioned dispersion compensation processing on the signal to which the apodization processing has been performed. Such processing is disclosed in, for example, Japanese Unexamined Patent Application Publication No. 2015-70919.

In general, if there is a difference between the dispersion characteristic of the measurement optical path and the dispersion characteristic of the reference optical path, the point spread function (hereinafter referred to as PSF) determined from the interference signal becomes dull and the S/N ratio decreases, which results in degradation of the image quality of the OCT image. In the present embodiment, the dispersion member 150 is disposed in the reference optical path so as to compensate for the difference between the dispersion characteristic of the measurement optical path and the dispersion characteristic of the reference optical path. Accordingly, when generating an OCT image in a depth range narrower than the full range, it is possible to detect the interference signal with a high S/N ratio and acquire an OCT image with high image quality.

Figure 5A:
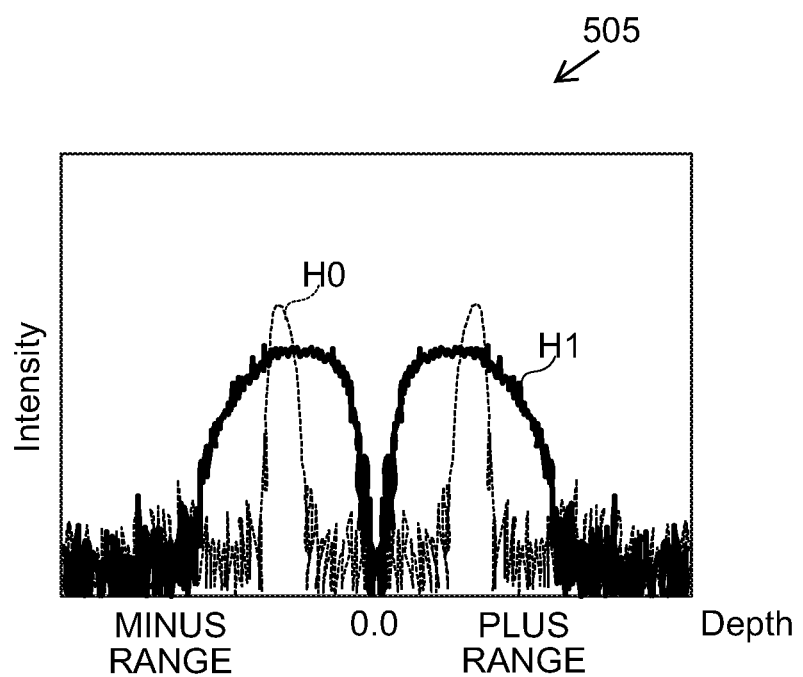
FIG. 5A is a diagram describing an operation of the OCT apparatus according to the embodiment.
Figure 5B:
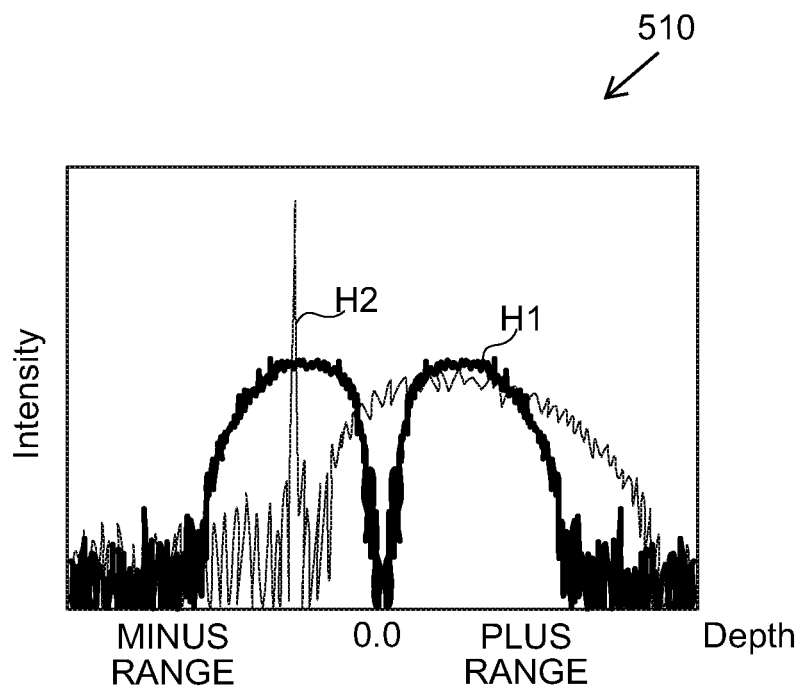
FIG. 5B is a diagram describing an operation of the OCT apparatus according to the embodiment.
Figure 5C:
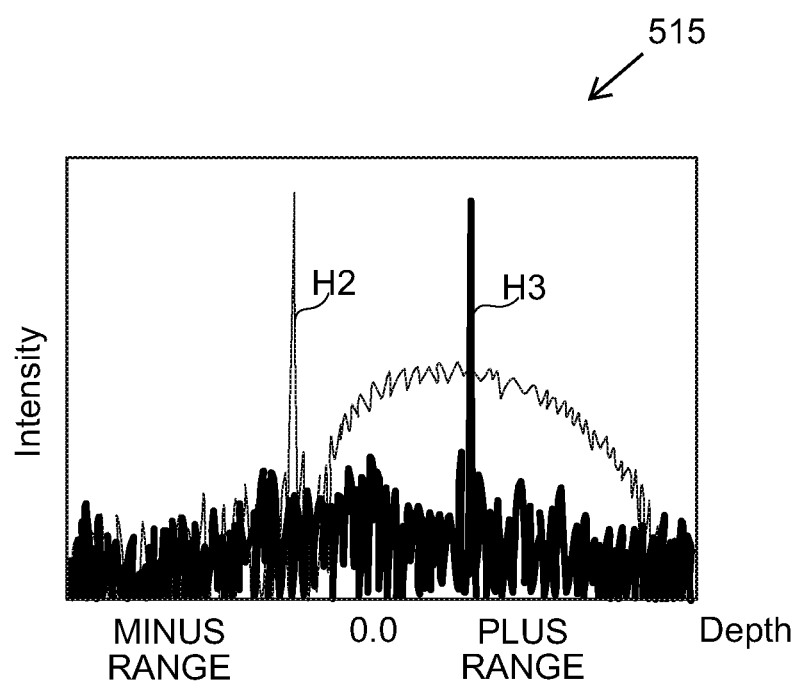
FIG. 5C is a diagram describing an operation of the OCT apparatus according to the embodiment.

FIG. 5A to FIG. 5C show diagrams 505, 510, and 515, respectively, describing the operation of the ophthalmic apparatus 1 according to the present embodiment. FIG. 5A to FIG. 5C show examples of the PSF determined from the interference signal obtained by the detector 125 in the full range OCT mode.

When the operation mode is set to the full range OCT mode, the main controller 211 controls the movement mechanism 80A to dispose the dispersion member 80 in the measurement optical path, and controls the movement mechanism 150A to remove the dispersion member 150 from the reference optical path. With this, the difference between the dispersion characteristic of the measurement optical path and the dispersion characteristic of the reference optical path becomes large. In this case, the waveform of the PSF of the interference signal obtained by the detector 125 (e.g., the waveform H1 shown in FIG. 5A) is duller than the waveform of the PSF of the interference signal detected in the standard OCT mode (e.g., the waveform H0 shown in FIG. 5A). The image forming unit 220 performs known dispersion compensation processing on the interference signal obtained by the detector 125 so that the waveform of the PSF of the interference signal on the minus range side becomes steep (e.g., the waveform H2 shown in FIG. 5B), for example. Subsequently, the image forming unit 220 detects and removes the interference signal on the minus range side where the waveform has become steep, and performs the above-described dispersion compensation processing in which the sign is inverted on the remaining interference signal on the plus range side (e.g., the waveform H3 shown in FIG. 5C). Next, the image forming unit 220 performs a known FFT process on the signal to which the dispersion compensation processing has been applied, and assigns brightness values to the generated amplitude components to form a full range OCT image.

Figure 6:
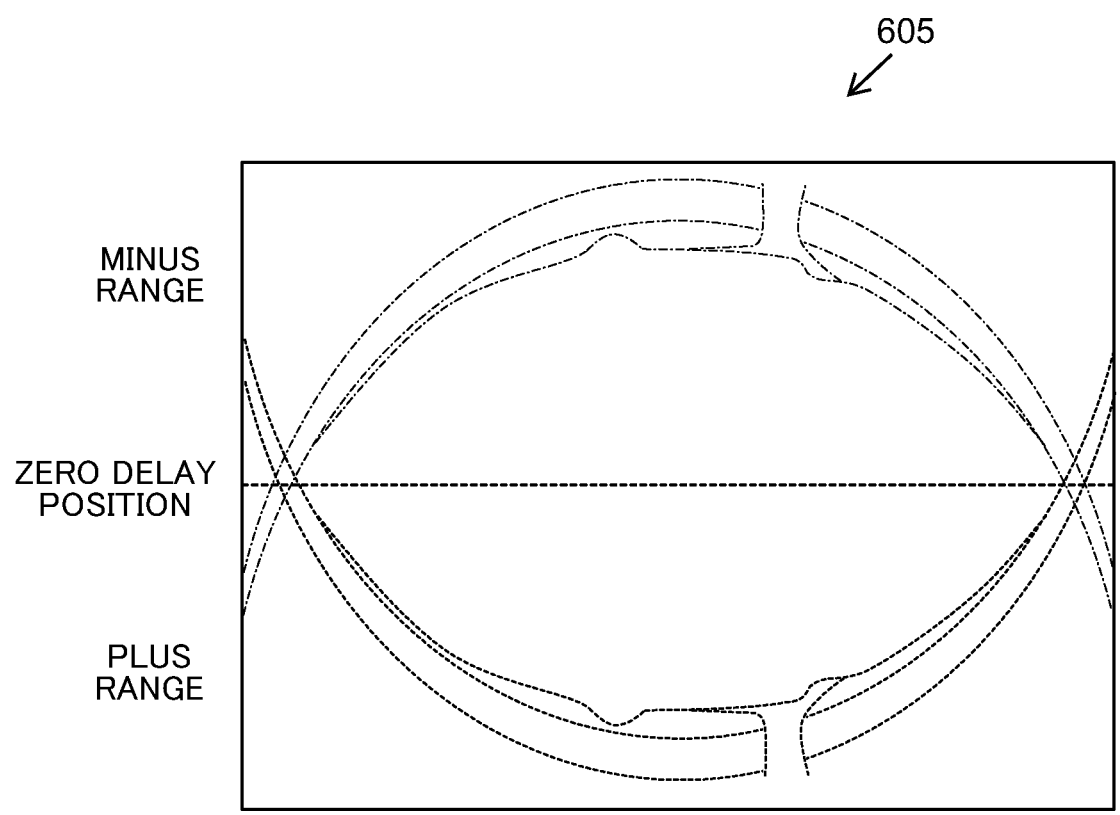
FIG. 6 is a diagram describing an operation of the OCT apparatus according to the embodiment.

In order to improve the image quality of the OCT image, the improvement of the S/N ratio of the interference signal is necessary. In order to improve the S/N ratio, any of the following is necessary: increasing the light amount of the measurement light LS incident on the subject's eye E; improving the light reception efficiency of the interference light LC with the detector 125; and suppressing the light amount loss of the OCT optical system. However, considering the safety of the subject, the amount of light incident on the subject's eye E is limited, and the improvement in the light reception efficiency of the interference light LC with the detector 125 is also limited. Therefore, it can be thought that the suppression of the light amount loss of the OCT optical system is most effective for improving the image quality of the OCT image. In the present embodiment, when an OCT image is formed in the full range, the dispersion amount of the dispersion member 80 disposed in the measurement optical path as described above is set to be equal to or larger than 30π radians when the optical path length difference caused by the chromatic dispersion between the reference optical path and the measurement optical path is converted into the phase difference. When the dispersion amount of the dispersion member 80 is small, for example, as shown in FIG. 6 in OCT image 605 describing an operation of the OCT apparatus according to the embodiment, a mirror image is depicted in the formed OCT image 605. On the other hand, according to the present embodiment, it is easy to detect the interference signal appearing on one range side with respect to the zero delay position while suppressing the light amount loss of the measurement light.

Figure 7:
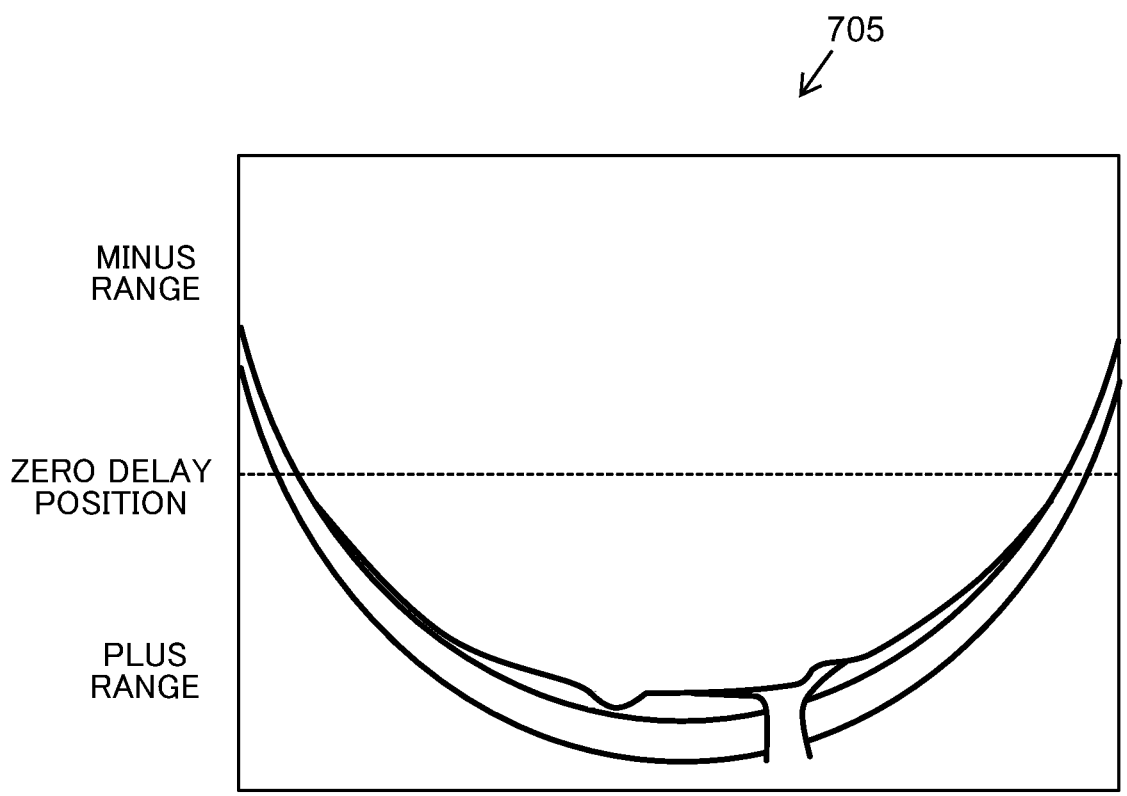
FIG. 7 is a diagram describing an operation of the OCT apparatus according to the embodiment.

Thus, an OCT image 705 of a high image quality in the full range can be acquired as shown in FIG. 7.

The dispersion member 80, the movement mechanism 80A, the dispersion member 150, and the movement mechanism 150A are an example of the "dispersion unit" which relatively changes the dispersion characteristics of the measurement optical path and the dispersion characteristics of the reference optical path according to the operation mode in the present embodiment. The dispersion member 80 is an example of the "first dispersion member" according to the present embodiment. The movement mechanism 80A is an example of the "first movement mechanism" according to the present embodiment. The dispersion member 150 is an example of the "second dispersion member" according to the present embodiment. The movement mechanism 150A is an example of the "second movement mechanism" according to the present embodiment. The standard OCT mode is an example of the "first operation mode" according to the present embodiment. The full range OCT mode is an example of the "second operation mode" according to the present embodiment. The arithmetic and control unit 200 is an example of the "information generation unit" that generates information on the object according to the operation mode, based on the detection result of the interference light in the present embodiment. The operation unit 242 is an example of the "selection unit" according to the present embodiment.

OPERATION EXAMPLES

The operation of the ophthalmic apparatus 1 according to the present embodiment will be described.

Figure 8:
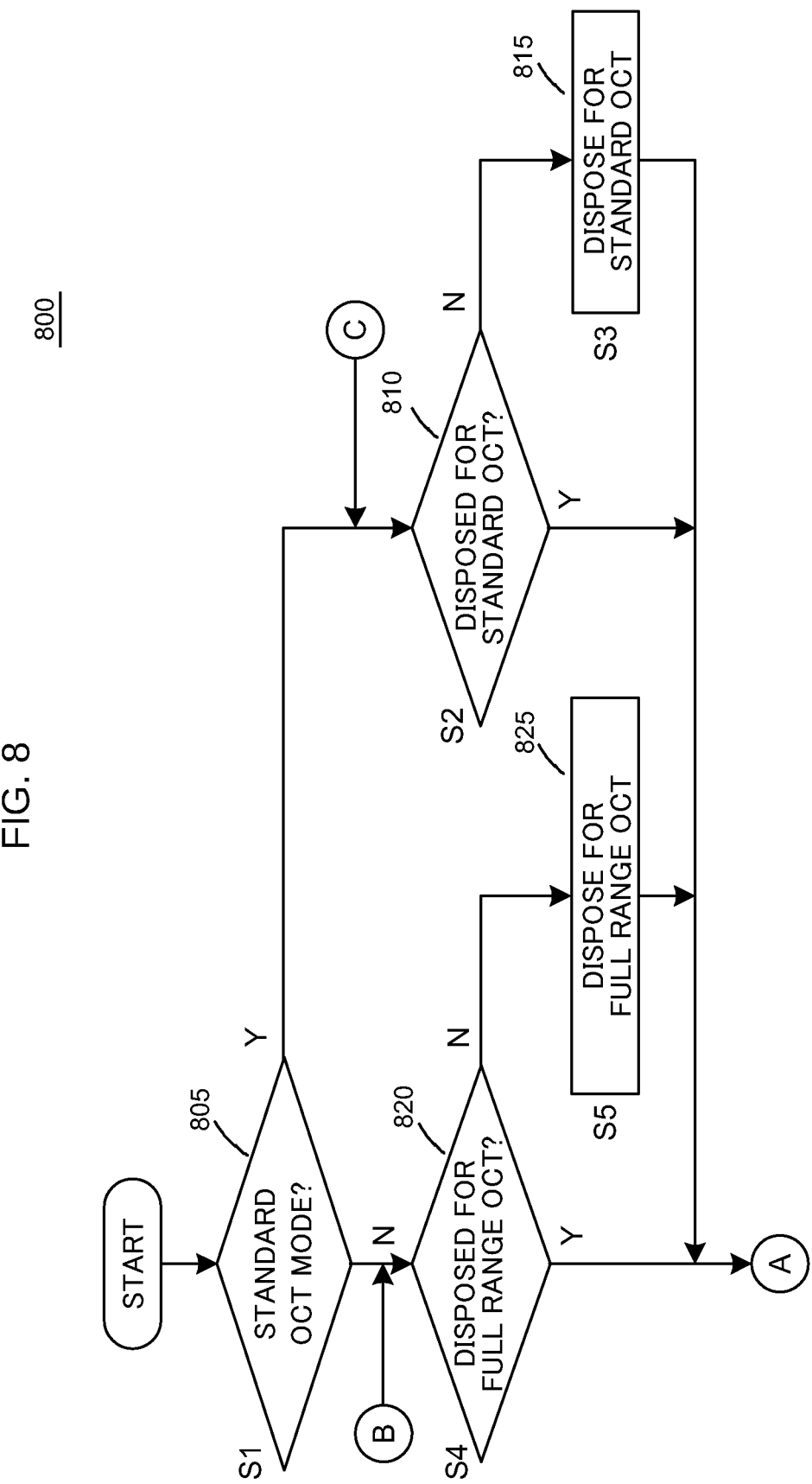
FIG. 8 is a flow chart of an operation example of the OCT apparatus according to the embodiment.
Figure 9:
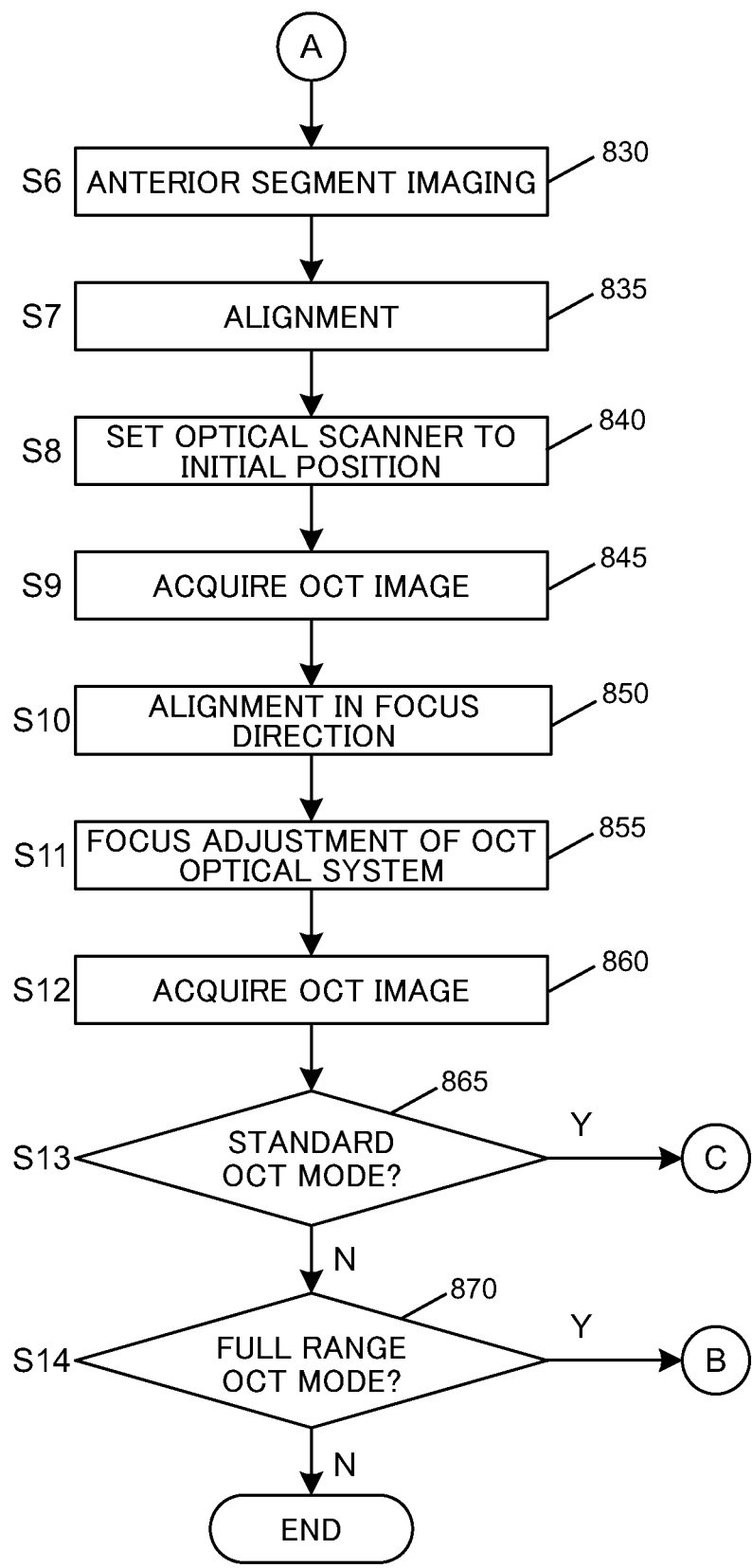
FIG. 9 is a flow chart of an operation example of the OCT apparatus according to the embodiment.

FIG. 8 and FIG. 9 show an example of the operation of the ophthalmic apparatus 1 according to the present embodiment. FIG. 8 and FIG. 9 show a flow chart 800 of an operation example in the case of acquiring an OCT image of the subject's eye E.

(Step 805 Also Referred to Herein as S1)

First, the main controller 211 determines whether or not the operation mode of the ophthalmic apparatus 1 is set to the standard OCT mode. For example, the storage unit 212 stores operation mode information indicating setting contents of operation modes of the ophthalmic apparatus 1. By referring to the operation mode information stored in the storage unit 212, the main controller 211 can determine whether or not the operation mode of the ophthalmic apparatus 1 is set to the standard OCT mode.

When it is determined that the operation mode is set to the standard OCT mode (S1: Y), the operation of the ophthalmic apparatus 1 proceeds to the step S2. When it is determined that the operation mode is not set to the standard OCT mode (S1: N), the operation of the ophthalmic apparatus 1 proceeds to the step S4.

(Step 810 also referred to herein as S2)

When it is determined in the step S1 that the operation mode is set to the standard OCT mode (S1: Y), the main controller 211 determines whether or not the dispersion members 80 and 150 are disposed for the standard OCT imaging. The main controller 211 may be configured to determine whether or not the dispersion members 80 and 150 are disposed for the standard OCT imaging by referring to the control contents for the movement mechanisms 80A and 150A. In another example, a sensor for detecting the insertion and removal states of the dispersion members 80 and 150 with respect to the optical paths may be provided, and the main controller 211 may be configured to determine whether or not the dispersion members 80 and 150 are disposed for the standard OCT imaging based on the detection signal from the sensor.

When it is determined that the dispersion members 80 and 150 are disposed for the standard OCT imaging (S2: Y), the operation of the ophthalmic apparatus 1 proceeds to the step S6. When it is determined that the dispersion members 80 and 150 are not disposed for the standard OCT imaging (S2: N), the operation of the ophthalmic apparatus 1 proceeds to the step S3.

(Step 815 Also Referred to Herein as S3)

When it is determined in the step S2 that the dispersion members 80 and 150 are not disposed for the standard OCT imaging (S2: N), the main controller 211 controls the movement mechanism 80A to remove the dispersion member 80 from the measurement optical path and controls the movement mechanism 150A to dispose the dispersion member 150 in the reference optical path. Then, the operation of the ophthalmic apparatus 1 proceeds to the step S6.

(Step 820 Also Referred to Herein as S4)

When it is determined in the step S1 that the operation mode is not set to the standard OCT mode (S1: N), the main controller 211 determines that the operation mode is set to the full range OCT mode. The main controller 211 then determines whether or not the dispersion members 80 and 150 are disposed for the full range OCT imaging. By referring to the control contents for the movement mechanisms 80A and 150A, the main controller 211 can judge whether or not the dispersion members 80 and 150 are disposed for the full range OCT imaging. In another example, as described above, a sensor for detecting the insertion and removal state of the dispersion members 80 and 150 with respect to the optical path may be provided, and the main controller 211 may be configured to determine whether or not the dispersion members 80 and 150 are disposed for the full range OCT imaging based on the detection signal from the sensor.

When it is determined that the dispersion members 80 and 150 are disposed for the full range OCT imaging (S4: Y), the operation of the ophthalmic apparatus 1 moves to the steps S6. When it is determined that the dispersion members 80 and 150 are not disposed for the full range OCT imaging (S4: N), the operation of the ophthalmic apparatus 1 proceeds to the step S5.

(Step 825 Also Referred to Herein as S5)

When it is determined in the step S4 that the dispersion members 80 and 150 are not disposed for the full range OCT imaging (S4: N), the main controller 211 controls the movement mechanism 80A to dispose the dispersion member 80 in the measurement optical path, and controls the movement mechanism 150A to remove the dispersion member 150 from the reference optical path. The operation of the ophthalmic apparatus 1 proceeds to the step S6.

(Step 830 Also Referred to Herein as S6)

The main controller 211 images the anterior segment of the subject's eye E using the photographing optical system 30 to acquire an anterior segment image.

(Step 835 Also Referred to Herein as S7)

The main controller 211 controls the optical system driver described above based on the anterior segment image acquired in the step S6 to move the optical system in the three-dimensional fashion, thereby performing the position matching of the optical system with respect to the subject's eye E in the x direction, the y direction, and the z direction orthogonal to both the x direction and the y direction.

(Step 840 Also Referred to Herein as S8)

The main controller 211 moves the optical scanner 42 to a predetermined initial position.

(Step 845 Also Referred to Herein as S9)

The main controller 211 turns on the light source unit 101 and controls the optical scanner 42 to start scanning the fundus Ef of the subject's eye E with the measurement light LS based on the light L0 emitted from the light source unit 101. As described above, the image forming unit 220 forms an OCT image of the fundus Ef based on the detection result of the interference light obtained by the detector 1125 according to the operation mode.

(Step 850 Also Referred to Herein as S10)

The main controller 211 performs alignment in the focus direction of the retina based on the anterior segment image obtained by the photographing optical system 30. With this, it becomes possible to finely adjust the position of the optical system provided in the OCT unit 100 in the optical axis direction.

(Step 855 Also Referred to Herein as S11)

Based on the detection signal of the interference light obtained by the OCT optical system, the main controller 211 changes the focus position of the optical system of the OCT unit 100. The main controller 211 changes the focus position of the optical system, for example, by moving the OCT focusing lens 43 in the optical axis direction so that the amplitude of the detection signal of a predetermined interference light becomes maximum.

(Step 860 Also Referred to Herein as S12)

Figure 10:
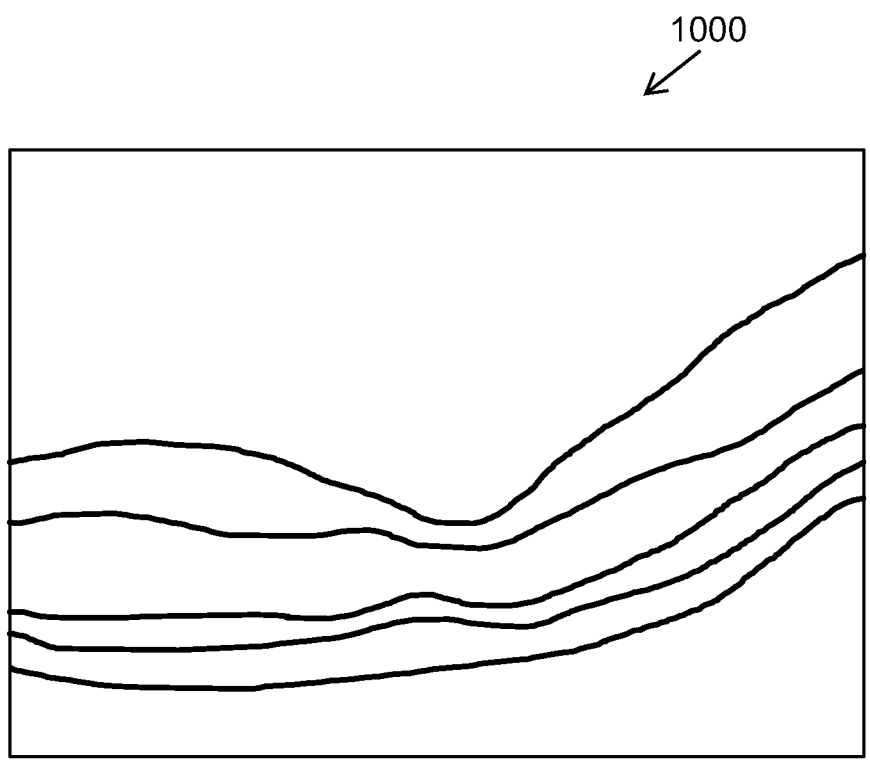
FIG. 10 is a diagram describing an operation of the OCT apparatus according to the embodiment.

Once again, by controlling the optical scanner 42, the main controller 211 starts scanning the fundus Ef of the subject's eye E with the measurement light LS based on the light L0 emitted from the light source unit 101. The image forming unit 220 forms an OCT image of the fundus Ef based on the detection result of the interference light obtained by the detector 125. When the operation mode is set to the full range OCT mode, an OCT image as shown in FIG. 7 is formed. When the operation mode is set to the standard OCT mode, an OCT image 1000 as shown in FIG. 10 is formed (i.e., describing an operation of the OCT apparatus according to the embodiment).

(Step 865 Also Referred to Herein as S13)

The main controller 211 determines whether or not to perform the next imaging in the standard OCT mode. For example, the main controller 211 can determine whether or not to perform the next imaging in the standard OCT mode, based on the operation contents input by the user through the operation unit 242.

When it is determined that the next imaging is to be performed in the standard OCT mode (S13: Y), the operation of the ophthalmic apparatus 1 moves to the step S2. When it is determined that the next imaging is not to be performed in the standard OCT mode (S13: N), the operation of the ophthalmic apparatus 1 moves to the step S14.

(Step 870 also referred to herein as S14)

When it is determined in the step S13 that the next imaging is not to be performed in the standard OCT mode (S13: N), the main controller 211 determines whether or not to perform the next imaging in the full range OCT mode. For example, the main controller 211 can determine whether or not to perform the next imaging in the full range OCT mode, based on the operation contents input by the user through the operation unit 242.

When it is determined that the next imaging is to be performed in the full range OCT mode (S14: Y), the operation of the ophthalmic apparatus 1 moves to the step S4. When it is determined that the next imaging is not to be performed in the full range OCT mode (S14: N), the operation of the ophthalmic apparatus 1 ends (END).

[Modification]

Described in the above embodiment is the case of performing the insertion and removal control of the dispersion members 80 and 150 as shown in FIG. 4 according to the operation mode. However, the insertion and removal control of the dispersion members 80 and 150 according to the above embodiment is not limited to this. For example, in order to simplify the design and control of the optical system, it is possible to dispose or insert and remove the dispersion members 80 and 150 according to the above embodiment as follows. Hereinafter, the insertion and removal control of the dispersion members 80 and 150 according to the modification of the above embodiment will be described focusing on differences from the above embodiment.

Figure 11:
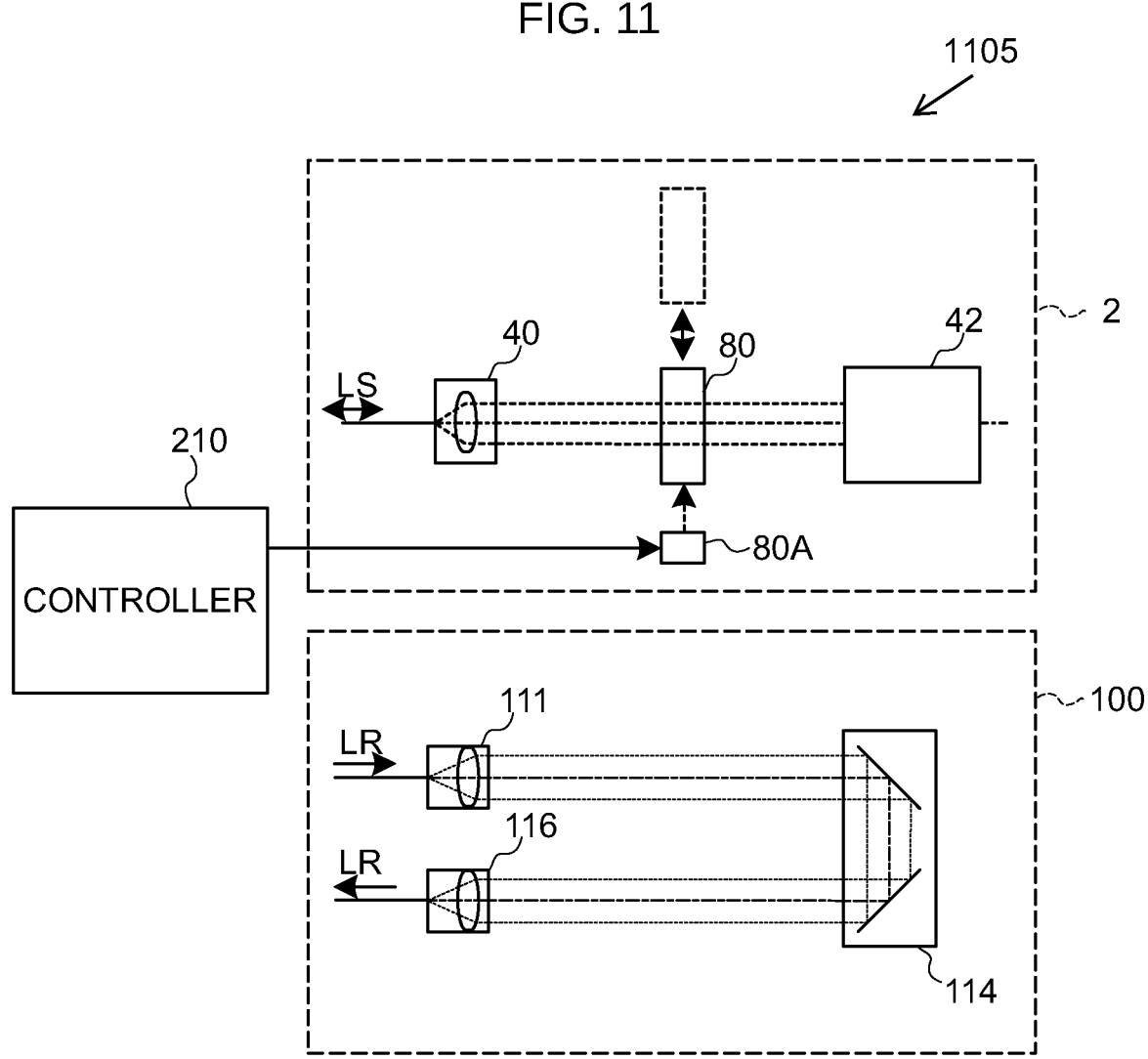
FIG. 11 is a diagram describing the OCT apparatus according to a modification of the embodiment.

FIG. 11 is a diagram 1105 describing the insertion and removal control according to the first modification of the above embodiment. In FIG. 11, parts similar to those in FIG. 4 are denoted by the same reference symbols, and description thereof is omitted as appropriate.

In the case where the difference between the dispersion characteristic of the measurement optical path in which the dispersion member 80 is not disposed and the dispersion characteristic of the reference optical path is compensated, it is not necessary to insert nor remove the dispersion member 150 into or from the reference optical path. For example, when the dispersion compensation processing is performed numerically by the image forming unit 220 or the like, or when the optical system is designed in advance so as to compensate for the difference between the dispersion characteristics, it is sufficient only to insert or remove the dispersion member 80 into or from the measurement optical path as shown in FIG. 11. For example, when the operation mode is set to the standard OCT mode, the controller 210 (e.g., the main controller 211) controls the movement mechanism 80A to remove the dispersion member 80 from the measurement optical path. When the operation mode is set to the full range OCT mode, the controller 210 (e.g., the main controller 211) controls the movement mechanism 80A to dispose the dispersion member 80 in the measurement optical path.

The standard OCT mode is an example of the "first operation mode" according to the present modification. The full range OCT mode is an example of the "second operation mode" according to the present modification.

Figure 12:
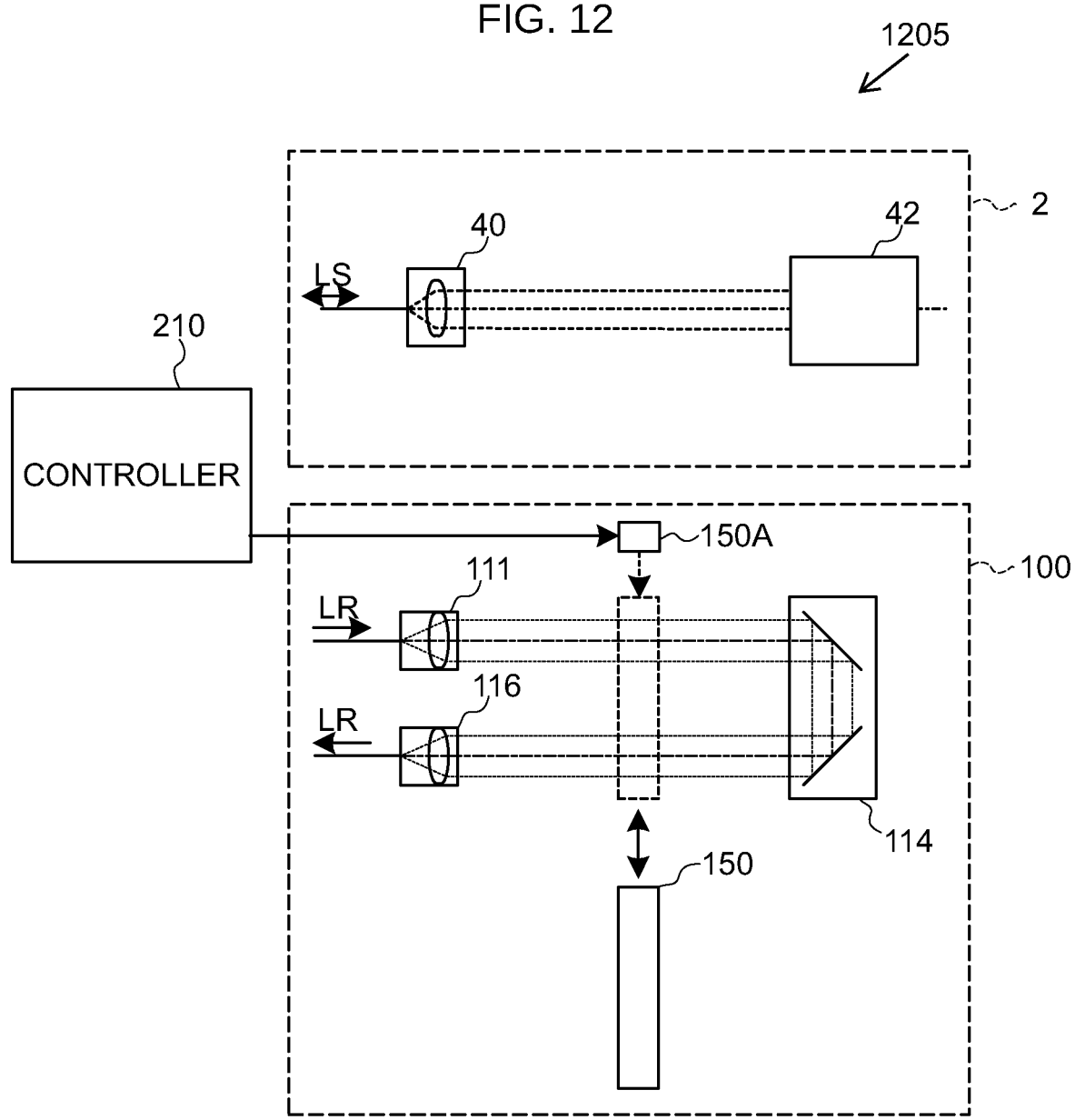
FIG. 12 is a diagram describing the OCT apparatus according to a modification example of the embodiment.

FIG. 12 is a diagram 1205 describing the insertion and removal control according to the second modification of the above embodiment. In FIG. 12, parts similar to those in FIG. 4 are denoted by the same reference symbols, and description thereof is omitted as appropriate.

For example, when the optical system is designed such that a predetermined dispersion amount is given in advance to the measurement optical path in which the dispersion member 80 is not disposed, it is not necessary to insert nor remove the dispersion member 80 into or from the measurement optical path. In this case, as shown in FIG. 12, it is sufficient only to insert or remove the dispersion member 150 into or from the reference optical path. The dispersion amount of the dispersion member 150 may be the dispersion amount of the dispersion member 80 according to the above embodiment. For example, when the operation mode is set to the full range OCT mode, the controller 210 (e.g., the main controller 211) controls the movement mechanism 150A to remove the dispersion member 150 from the reference optical path. When the operation mode is set to the standard OCT mode, the controller 210 (e.g., the main controller 211) controls the movement mechanism 150A to dispose the dispersion member 150 in the reference optical path.

The full range OCT mode is an example of the "first operation mode" according to the present modification. The standard OCT mode is an example of the "second operation mode" according to the present modification.

Figure 13:
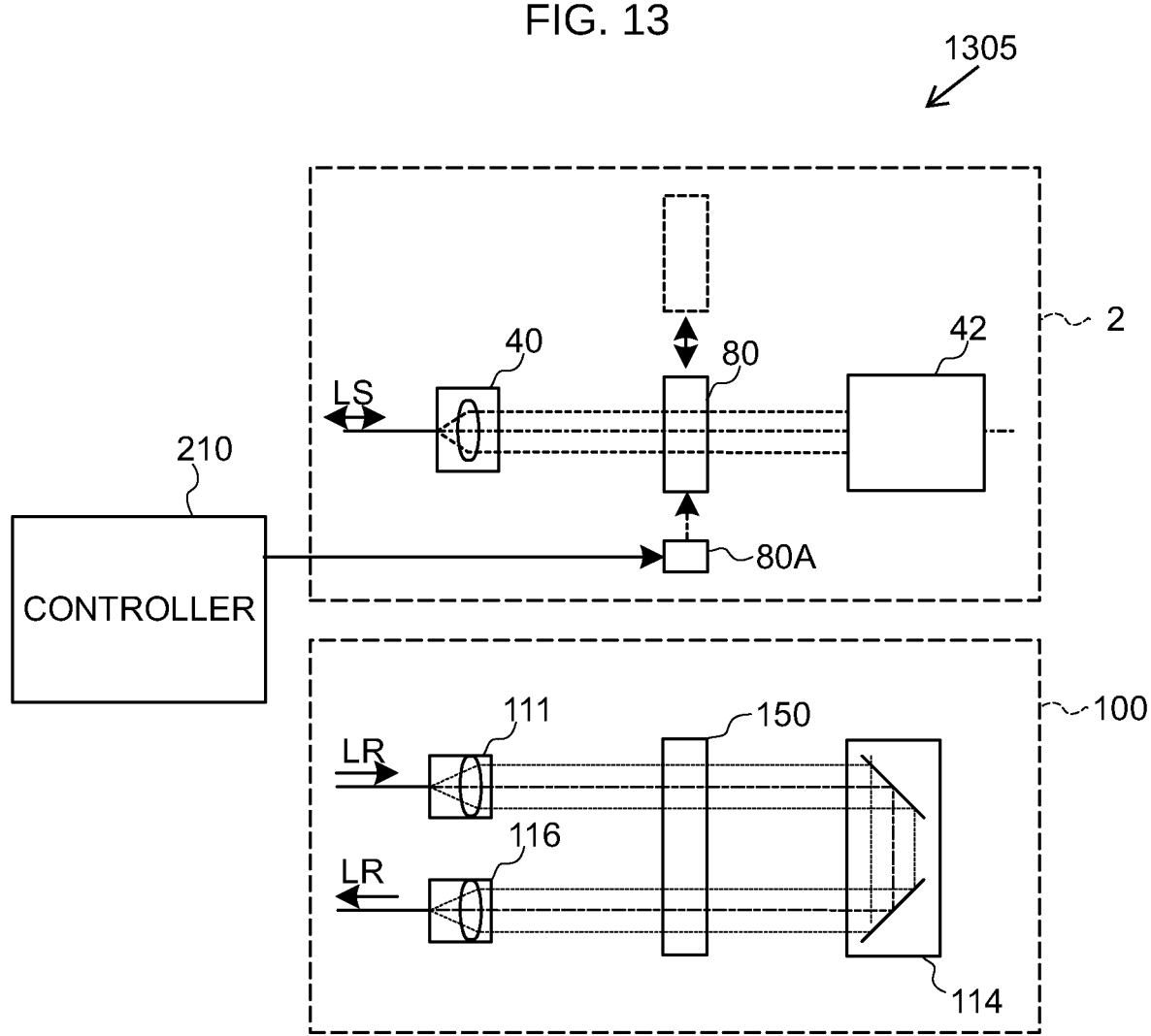
FIG. 13 is a diagram describing the OCT apparatus according to a modification example of the embodiment.

FIG. 13 is a diagram 1305 describing the insertion and removal control according to the third modification of the above embodiment. In FIG. 13, parts similar to those in FIG. 4 are denoted by the same reference symbols, and description thereof is omitted as appropriate.

For example, the dispersion member 80 may be inserted into or removed from the measurement optical path while the dispersion member 150 is disposed in the reference optical path. The dispersion member 80 gives a predetermined dispersion amount to the measurement optical path. The movement mechanism 80A inserts and removes the dispersion member 80 into and from the measurement optical path. The dispersion member 150 is disposed in the reference optical path and compensates for the difference between the dispersion characteristic of the measurement optical path in which the dispersion member 80 is not disposed and the dispersion characteristic of the reference optical path. In the present modification, the dispersion amount of the dispersion member 80 may be a combined amount of: a dispersion amount that compensates for the difference between the dispersion characteristic of the measurement optical path and the dispersion characteristic of the reference optical path; and a dispersion amount that is equal to or larger than $30\pi$ radians when the optical path length difference caused by chromatic dispersion between the reference optical path and the measurement optical path is converted into a phase difference. For example, when the operation mode is set to the standard OCT mode, the controller 210 (e.g., the main controller 211) controls the movement mechanism 80A to remove the dispersion member 80 from the measurement optical path. When the operation mode is set to the full range OCT mode, the controller 210 (e.g., the main controller 211) controls the movement mechanism 80A to dispose the dispersion member 80 in the measurement optical path.

The standard OCT mode is an example of the "first operation mode" according to the present modification. The full range OCT mode is an example of the "second operation mode" according to the present modification.

Figure 14:
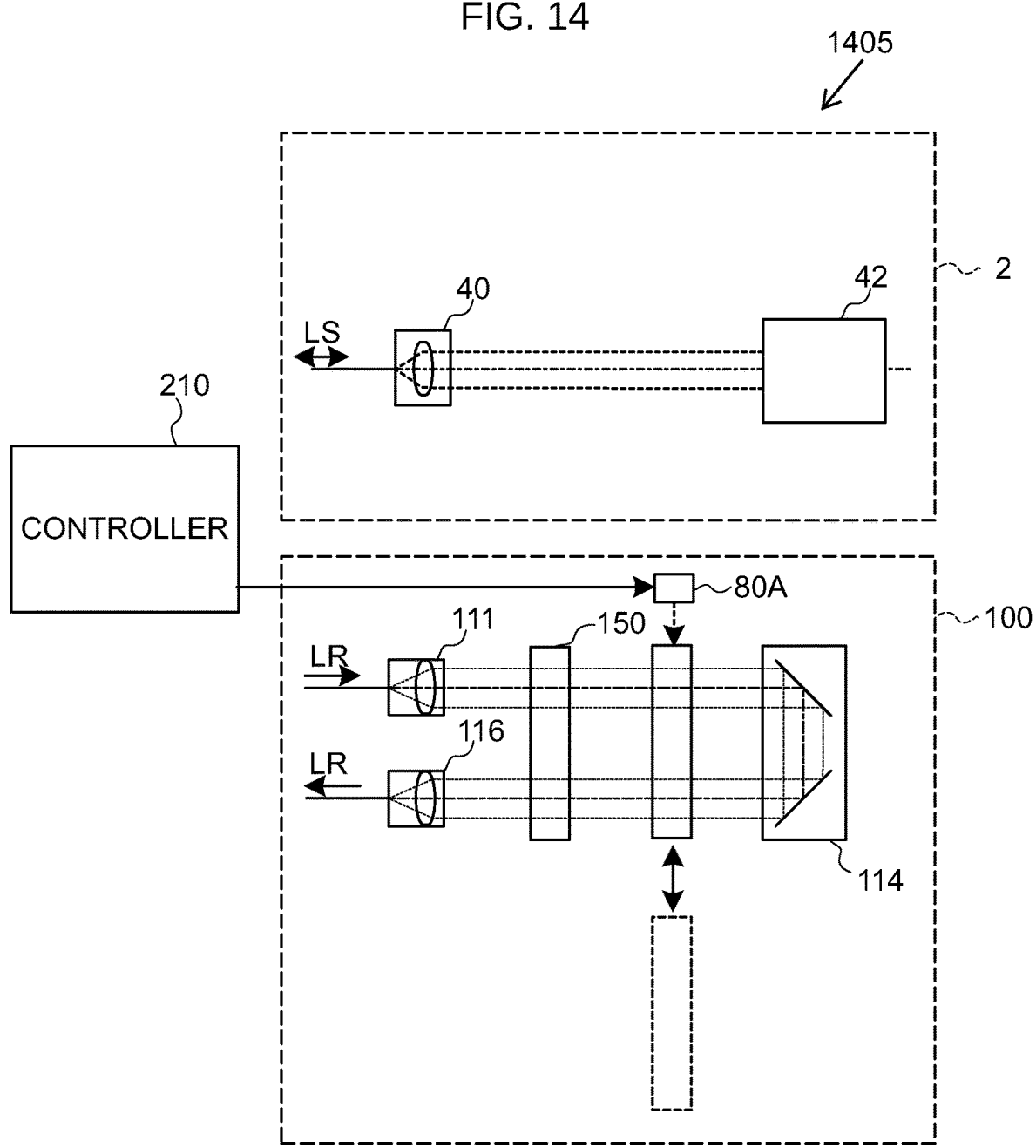
FIG. 14 is a diagram describing the OCT apparatus according to a modification example of the embodiment.

FIG. 14 is a diagram 1405 describing the insertion and removal control according to the fourth modification of the embodiment. In FIG. 14, parts similar to those in FIG. 4 are denoted by the same reference symbols, and description thereof is omitted as appropriate.

For example, the dispersion member 80 may be inserted into or removed from the reference optical path while the dispersion member 150 is disposed in the reference optical path. The dispersion member 80 gives a predetermined dispersion amount to the reference optical path. The movement mechanism 80A inserts and removes the dispersion member 80 into and from the reference optical path. The dispersion member 150 is disposed in the reference optical path and compensates for the difference between the dispersion characteristic of the measurement optical path in which the dispersion member 80 is not disposed and the dispersion characteristic of the reference optical path. For example, when the operation mode is set to the standard OCT mode, the controller 210 (e.g., the main controller 211) controls the movement mechanism 80A to remove the dispersion member 80 from the reference optical path. When the operation mode is set to the full range OCT mode, the controller 210 (e.g., the main controller 211) controls the movement mechanism 80A to dispose the dispersion member 80 in the reference optical path.

The standard OCT mode is an example of the "first operation mode" according to the present modification. The full range OCT mode is an example of the "second operation mode" according to the present modification.

[Effects]

The effects of the OCT apparatus applied to the ophthalmic apparatus according to an embodiment (e.g., the above embodiment or its modification) will be described.

The OCT apparatus according to the embodiment is configured to split light (L0) emitted from a light source (the light source unit 101) into measurement light (LS) and reference light (LR), project the measurement light on the object (the subject's eye E), and detect interference light (LC) generated from the reference light and the measurement light returning from the object. The OCT apparatus includes a dispersion unit (80, 80A, 150 and 150A) and an information generation unit (the arithmetic and control unit 200). The dispersion unit is configured to relatively change the dispersion characteristic of the measurement optical path which is the optical path of the measurement light and the dispersion characteristic of the reference optical path which is an optical path of the reference light, according to the operation mode corresponding to a depth range. The information generation unit is configured to generate information (e.g., a cross sectional image) on the object according to the operation mode, based on the detection result of the interference light.

According to such a configuration, the dispersion characteristic of the measurement optical path and the dispersion characteristic of the reference optical path are relatively changed in accordance with the operation mode corresponding to the depth range, and the information on the object corresponding to the concerned operation mode is generated. Therefore, it is possible to acquire information on the object with the depth range corresponding to the operation mode. This makes it possible to acquire information on the object with a high S/N ratio in a narrow depth range and information on the object in the full range with a simple configuration.

In the OCT apparatus according to the embodiment, the dispersion unit may include a first dispensation member (80), a first movement mechanism (80A), a second dispense member (150), and a second movement mechanism (150A). The first dispersion member gives a first dispersion amount to the measurement optical path to increase the difference between the dispersion characteristic of the measurement optical path and the dispersion characteristic of the reference optical path. The first movement mechanism inserts and removes the first dispersion member into and from the measurement optical path. The second dispersion member compensates for the difference between the dispersion characteristic of the measurement optical path in which the first dispersion member is not disposed and the dispersion characteristic of the reference optical path. The second movement mechanism inserts and removes the second dispersion member into and from the reference optical path.

According to such a configuration, as shown in FIG. 4, the dispersion characteristic of the measurement optical path and the dispersion characteristic of the reference optical path are relatively changed by inserting and removing the first disposition member and the second disposition member. Therefore, it is possible to acquire highly accurate information on the object while simplifying the design of the optical system.

The OCT apparatus according to the embodiment may further include a controller (210) configured as follows. In a first operation mode, the controller controls the first movement mechanism to remove the first dispersion member from the measurement optical path, and controls the second movement mechanism to dispose the second dispersion member in the reference optical path. In addition, in a second operation mode, the controller controls the first movement mechanism to dispose the first dispersion member in the measurement optical path, and controls the second movement mechanism to remove the second dispersion member from the reference optical path.

According to such a configuration, the controller that controls the first movement mechanism and the second movement mechanism is provided. Therefore, it becomes easy to acquire highly accurate information on the object according to the operation mode.

Further, in the OCT apparatus according to the embodiment, the dispersion unit may include a first dispersion member (80) and a first movement mechanism (80A). The first dispersion member gives a first dispersion amount to the measurement optical path to increase the difference between the dispersion characteristic of the measurement optical path and the dispersion characteristic of the reference optical path. The first movement mechanism inserts and removes the first dispersion member into and from the measurement optical path.

According to such a configuration, as shown in FIG. 11, the dispersion characteristic of the measurement optical path and the dispersion characteristic of the reference optical path can be relatively changed only by inserting and removing the first dispersion member into and from the measurement optical path. Therefore, it is possible to acquire highly accurate information on the object while simplifying the design and control of the optical system. For example, when the difference between the dispersion characteristic of the reference optical path and the dispersion characteristic of the measurement optical path in which the first dispersion member is not disposed is compensated (e.g., the case in which the dispersion compensation is performed by software processing, or the case in which the dispersion compensation is performed in advance through the design of optics), it is possible to simplify the design and control of the optical system.

Also, the OCT apparatus according to the embodiment may include a controller (210) configured as follows. In a first operation mode, the controller controls the first movement mechanism to remove the first dispersion member from the measurement optical path. In addition, in a second operation mode, the controller controls the first movement mechanism to dispose the first dispersion member in the measurement optical path.

According to such a configuration, the controller that controls the first movement mechanism is provided. Therefore, it becomes easy to obtain highly accurate information on the object according to the operation mode while simplifying control.

Further, in the OCT apparatus according to the embodiment, the dispersion unit may include a first dispersion member (150) and a first movement mechanism (150A). The first dispersion member gives a first dispersion amount to the reference optical path to increase the difference between the dispersion characteristic of the measurement optical path and the dispersion characteristic of the reference optical path. The first movement mechanism inserts and removes the first dispersion member into and from the reference optical path.

According to such a configuration, as shown in FIG. 12, the dispersion characteristic of the measurement optical path and the dispersion characteristic of the reference optical path are relatively changed only by inserting and removing the first dispersion member into and from the reference optical path. Therefore, it is possible to acquire highly accurate information on the object while simplifying the design and control of the optical system. For example, when a predetermined dispersion amount is already given to the measurement optical path in which a dispersion member is not disposed, it is possible to relatively change the dispersion characteristic of the measurement optical path and the dispersion characteristic of the reference optical path only by inserting and removing the first dispersion member into and from the reference optical path. This makes it possible to simplify the design and control of the optical system.

Also, the OCT apparatus according to the embodiment may include a controller (210) configured as follows. In a first operation mode, the controller controls the first movement mechanism to remove the first dispersion member from the reference optical path. In a second operation mode, the controller controls the first movement mechanism to dispose the first dispersion member in the reference optical path.

According to such a configuration, the controller that controls the first movement mechanism is provided. Therefore, it becomes easy to obtain highly accurate information on the object according to the operation mode while simplifying control.

Further, in the OCT apparatus according to the embodiment, the object may be a living eye. In addition, the first dispersion amount may be equal to or larger than 30π radians when the optical path length difference caused by chromatic dispersion between the reference optical path and the measurement optical path is converted into a phase difference.

According to such a configuration, the first dispersion member is configured to give the dispersion amount corresponding to the optical path length difference corresponding to the phase difference that is equal to or larger than 30π radians, and the first dispersion member thus configured is removably inserted into the optical path. Therefore, it becomes easy to detect the interference signal on any of the plus range and the minus range, and it becomes possible to acquire highly accurate information on the living eye in the full range.

In the OCT apparatus according to the embodiment, the dispersion unit may include a first dispersion member (80), a first movement mechanism (80A), and a second dispersion member (150). The first dispersion member gives a second dispersion amount to the measurement optical path. The first movement mechanism inserts and removes the first dispersion member into and from the measurement optical path. The second dispersion member is disposed in the reference optical path and compensates for the difference between the dispersion characteristic of the measurement optical path in which the first dispersion member is not disposed and the dispersion characteristic of the reference optical path.

According to such a configuration, as shown in FIG. 13, the first dispersion member is inserted into and removed from the measurement optical path while the second dispersion member that compensates for the difference between the dispersion characteristics of the two optical paths is disposed in the reference optical path. This makes it possible to generate highly accurate information on the object while simplifying the design and control of the optical system.

Further, the OCT apparatus according to the embodiment may include a controller (210) configured as follows. In a first operation mode, the controller controls the first movement mechanism to remove the first dispersion member from the measurement optical path. In addition, in a second operation mode, the controller controls the first movement mechanism to dispose the first dispersion member in the measurement optical path.

According to such a configuration, the controller that controls the first movement mechanism is provided. Therefore, it becomes easy to obtain highly accurate information on the object according to the operation mode while simplifying control.

In the OCT apparatus according to the embodiment, the object may be a living eye. In addition, the second dispersion amount may be a combined amount of: a dispersion amount that compensates for the difference between the dispersion characteristic of the measurement optical path and the dispersion characteristic of the reference optical path; and a dispersion amount that is equal to or larger than 30π radians when the optical path length difference caused by chromatic dispersion between the reference optical path and the measurement optical path is converted into a phase difference.

According to such a configuration, the first dispersion member is configured to give a combined amount of the dispersion amount that compensates for the difference between the dispersion characteristic of the measurement optical path and the dispersion characteristic of the reference optical path and the dispersion amount corresponding to the optical path length difference corresponding to the phase difference that is equal to or larger than 30π radians, and the first dispersion member thus configured is removably inserted into the optical path. Therefore, it becomes easy to detect the interference signal on any of the plus range and the minus range, and it becomes possible to acquire highly accurate information on the living eye in the full range.

In the OCT apparatus according to the embodiment, the dispersion unit may include a first dispersion member (80), a first movement mechanism (80A), and a second dispersion member (150). The first dispersion member gives a second dispersion amount to the reference optical path. The first movement mechanism inserts and removes the first dispersion member into and from the reference optical path. The second dispersion member is disposed in the reference optical path and compensates for the difference between the dispersion characteristic of the reference optical path in which the first dispersion member is not disposed and the dispersion characteristic of the measurement optical path.

According to such a configuration, as shown in FIG. 14, the first dispersion member is inserted into and removed from the reference optical path while the second dispersion member that compensates for the difference between the dispersion characteristics of the two optical paths is disposed in the reference optical path. This makes it possible to acquire highly accurate information on the object while simplifying the design of the optical system.

The OCT apparatus according to the embodiment further includes a controller (210) configured as follows. In a first operation mode, the controller controls the first movement mechanism to remove the first dispersion member from the reference optical path. In addition, in a second operation mode, the controller controls the first movement mechanism to dispose the first dispersion member in the reference optical path.

According to such a configuration, the controller that controls the first movement mechanism is provided. Therefore, it becomes easy to obtain highly accurate information on the object according to the operation mode while simplifying control.

The OCT apparatus according to the embodiment may further includes a collimator lens (the collimator lens in the collimator lens unit 40) and an optical scanner (42). The collimator lens is configured to convert the measurement light into a parallel light beam. The optical scanner is configured to deflect the measurement light made into the parallel light beam by the collimator lens. In addition, the first dispersion member may be disposed between the collimator lens and the optical scanner.

According to such a configuration, the first dispersion member can be disposed at a position between the collimator lens and the optical scanner in the measurement optical path. Therefore, it is possible to acquire highly accurate information on the object according to the operation mode without being affected by the deflection of the measurement light caused by the optical scanner.

In addition, the OCT apparatus according to the embodiment may include a selection unit (the operation unit 242) configured to select any of two or more operation modes corresponding to different depth ranges. In addition, the information generation unit may include an image forming unit (220) that forms a cross sectional image of the depth range corresponding to the operation mode selected by the selection unit.

According to such a configuration, a cross sectional image of the object is formed with the depth range corresponding to the operation mode selected by the selection unit. Therefore, it is possible to easily obtain cross sectional images of the object with high resolution over a desired depth range.

MODIFICATION EXAMPLES

The embodiment described above is merely an example for implementing the present invention. Those who intend to implement the present invention can apply arbitrary modification, omission, addition, or the like within the scope of the gist of the present invention.

In the above-described embodiment or the modification thereof, the case in which the arithmetic and control unit 200 forms a cross sectional image of the subject's eye E as the information of the subject's eye has been described. However, the invention is not limited to this. For example, the arithmetic and control unit 200 may be configured to measure the intraocular distance such as the axial length of the subject's eye E as the information of the subject's eye. More specifically, the OCT apparatus may be configured to measure the intraocular distance such as the axial length of the subject's eye E over the full range in the full range OCT mode, and form a cross sectional image of the subject's eye E in a range narrower than the full range in the standard OCT mode.

In the above-described embodiment or the modification thereof, the case where the configuration of the optical system in the ophthalmic apparatus to which the OCT apparatus according to the embodiment is employed is the configuration shown in FIG. 1 and FIG. 2 has been described. However, the configuration of the optical system is not limited to this. The optical system according to another embodiment may include an optical system to project a laser light beam on a treatment site in the eye fundus, an optical system to move a visual target in a state where the subject's eye is being fixated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An optical coherence tomography (OCT) apparatus that splits light from a light source into measurement light and reference light, projects the measurement light on an object, and detects interference light generated from the reference light and the measurement light returning from the object, the OCT apparatus comprising:
    a dispersion unit configured to relatively change a dispersion characteristic of a measurement optical path which is an optical path of the measurement light and a dispersion characteristic of a reference optical path which is an optical path of the reference light, according to an operation mode corresponding to a depth range; and
    an information generation unit configured to generate information on the object according to the operation mode, based on a detection result of the interference light.

2. The OCT apparatus of claim 1, wherein the dispersion unit comprises:
    a first dispersion member that gives a first dispersion amount to the measurement optical path to increase a difference between the dispersion characteristic of the measurement optical path and the dispersion characteristic of the reference optical path,
    a first movement mechanism that inserts and removes the first dispersion member into and from the measurement optical path,
    a second dispersion member that compensates for a difference between the dispersion characteristic of the measurement optical path in which the first dispersion member is not disposed and the dispersion characteristic of the reference optical path, and
    a second movement mechanism that inserts and removes the second dispersion member into and from the reference optical path.

3. The OCT apparatus of claim 2, further comprising a controller configured to control the first movement mechanism to remove the first dispersion member from the measurement optical path and control the second movement mechanism to dispose the second dispersion member in the reference optical path in a first operation mode, and control the first movement mechanism to dispose the first dispersion member in the measurement optical path and control the second movement mechanism to remove the second dispersion member from the reference optical path in a second operation mode.

4. The OCT apparatus of claim 2, wherein
    the object is a living eye, and
    the first dispersion amount is equal to or larger than 307 radians when an optical path length difference caused by chromatic dispersion between the reference optical path and the measurement optical path is converted into a phase difference.

5. The OCT apparatus of claim 2, further comprising:
a collimator lens configured to convert the measurement light into a parallel light beam; and
an optical scanner configured to deflect the measurement light made into the parallel light beam by the collimator lens,
wherein the first dispersion member can be disposed between the collimator lens and the optical scanner.

6. The OCT apparatus of claim 1, wherein the dispersion unit comprises:
a first dispersion member that gives a first dispersion amount to the measurement optical path to increase a difference between the dispersion characteristic of the measurement optical path and the dispersion characteristic of the reference optical path; and
a first movement mechanism that inserts and removes the first dispersion member into and from the measurement optical path.

7. The OCT apparatus of claim 6, further comprising a controller configured to control the first movement mechanism to remove the first dispersion member from the measurement optical path in a first operation mode, and control the first movement mechanism to dispose the first dispersion member in the measurement optical path in a second operation mode.

8. The OCT apparatus of claim 6, wherein
the object is a living eye, and
the first dispersion amount is equal to or larger than 307 radians when an optical path length difference caused by chromatic dispersion between the reference optical path and the measurement optical path is converted into a phase difference.

9. The OCT apparatus of claim 6, further comprising:
a collimator lens configured to convert the measurement light into a parallel light beam; and
an optical scanner configured to deflect the measurement light made into the parallel light beam by the collimator lens,
wherein the first dispersion member can be disposed between the collimator lens and the optical scanner.

10. The OCT apparatus of claim 1, wherein the dispersion unit comprises:
a first dispersion member that gives a first dispersion amount to the reference optical path to increase a difference between the dispersion characteristic of the measurement optical path and the dispersion characteristic of the reference optical path; and
a first movement mechanism that inserts and removes the first dispersion member into and from the reference optical path.

11. The OCT apparatus of claim 10, further comprising a controller configured to control the first movement mechanism to remove the first dispersion member from the reference optical path in a first operation mode, and control the first movement mechanism to dispose the first dispersion member in the reference optical path in a second operation mode.

12. The OCT apparatus of claim 10, wherein
the object is a living eye, and
the first dispersion amount is equal to or larger than 307 radians when an optical path length difference caused by chromatic dispersion between the reference optical path and the measurement optical path is converted into a phase difference.

13. The OCT apparatus of claim 10, further comprising:
a collimator lens configured to convert the measurement light into a parallel light beam; and
an optical scanner configured to deflect the measurement light made into the parallel light beam by the collimator lens,
wherein the first dispersion member can be disposed between the collimator lens and the optical scanner.

14. The OCT apparatus of claim 1, wherein the dispersion unit comprises:
a first dispersion member that gives a second dispersion amount to the measurement optical path,
a first movement mechanism that inserts and removes the first dispersion member into and from the measurement optical path, and
a second dispersion member that is disposed in the reference optical path and compensates for a difference between the dispersion characteristic of the measurement optical path in which the first dispersion member is not disposed and the dispersion characteristic of the reference optical path.

15. The OCT apparatus of claim 14, further comprising a controller configured to control the first movement mechanism to remove the first dispersion member from the measurement optical path in a first operation mode, and control the first movement mechanism to dispose the first dispersion member in the measurement optical path in a second operation mode.

16. The OCT apparatus of claim 14, wherein
the object is a living eye, and
the second dispersion amount is a combined amount of a dispersion amount that compensates for a difference between the dispersion characteristic of the measurement optical path and the dispersion characteristic of the reference optical path and a dispersion amount that is equal to or larger than 307 radians when an optical path length difference caused by chromatic dispersion between the reference optical path and the measurement optical path is converted into a phase difference.

17. The OCT apparatus of claim 14, further comprising:
a collimator lens configured to convert the measurement light into a parallel light beam; and
an optical scanner configured to deflect the measurement light made into the parallel light beam by the collimator lens,
wherein the first dispersion member can be disposed between the collimator lens and the optical scanner.

18. The OCT apparatus of claim 1, wherein the dispersion unit comprises:
a first dispersion member that gives a second dispersion amount to the reference optical path,
a first movement mechanism that inserts and removes the first dispersion member into and from the reference optical path, and
a second dispersion member that is disposed in the reference optical path and compensates for a difference between the dispersion characteristic of the reference optical path in which the first dispersion member is not disposed and the dispersion characteristic of the measurement optical path.

19. The OCT apparatus of claim 18, further comprising a controller configured to control the first movement mechanism to remove the first dispersion member from the reference optical path in a first operation mode, and control the first movement mechanism to dispose the first dispersion member in the reference optical path in a second operation mode.

20. The OCT apparatus of claim 18, further comprising:
a collimator lens configured to convert the measurement light into a parallel light beam; and an optical scanner configured to deflect the measurement light made into the parallel light beam by the collimator lens, wherein the first dispersion member can be disposed between the collimator lens and the optical scanner.

* * * * *